(12) United States Patent
Grondahl et al.

(10) Patent No.: US 6,759,400 B2
(45) Date of Patent: *Jul. 6, 2004

(54) MEIOSIS REGULATING COMPOUNDS

(75) Inventors: Christian Grondahl, Vaerlose (DK);
Frederik Christian Gronvald, Vedbaek (DK); Peter Faarup, Vaerlose (DK);
Anthony Murray, Hellerup (DK); Jan Lund Ottesen, Vaerlose (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 10/242,381

(22) Filed: Sep. 11, 2002

(65) Prior Publication Data

US 2003/0032824 A1 Feb. 13, 2003

Related U.S. Application Data

(63) Continuation of application No. 09/764,203, filed on Jan. 17, 2001, now Pat. No. 6,486,145, which is a continuation of application No. 09/333,391, filed on Jun. 15, 1999, now abandoned, which is a continuation of application No. PCT/DK97/00584, filed on Dec. 19, 1997.
(60) Provisional application No. 60/041,488, filed on Feb. 11, 1997.

(30) Foreign Application Priority Data

Dec. 20, 1996 (DK) .................................. 961478

(51) Int. Cl.$^7$ ............................................... A61K 31/56
(52) U.S. Cl. ........................ 514/182; 514/177; 514/178
(58) Field of Search ........................ 552/540; 514/182, 514/177, 178

(56) References Cited

U.S. PATENT DOCUMENTS

| 3,931,403 | A | 1/1976 | Saltzman |
| 4,011,250 | A | 3/1977 | Ishikawa et al. |
| 4,254,045 | A | 3/1981 | DeLuca et al. |
| 4,329,295 | A | 5/1982 | Chorvat |
| 4,670,190 | A | 6/1987 | Hesse et al. |
| 5,830,757 | A | 11/1998 | Guddal et al. ............. 435/325 |

FOREIGN PATENT DOCUMENTS

| DE | 1 183 079 | 12/1964 |
| DE | 1 224 738 | 9/1966 |
| DE | 22 01 991 | 8/1972 |
| DE | 22 36 778 | 2/1973 |
| DE | 2 409 971 | 9/1974 |
| DE | 2 415 676 | 10/1974 |
| DE | 24 53 648 | 5/1975 |
| DE | 25 46 715 | 4/1976 |
| DE | 28 22 486 | 12/1978 |
| DE | 32 41 172 | 5/1983 |
| DE | 3390016 | 5/1984 |
| DK | 123767 | 12/1972 |
| DK | 144264 | 7/1974 |
| EP | 0 015 122 | 9/1980 |
| EP | 00 63 678 | 11/1982 |
| EP | 0 322 036 | 6/1989 |
| EP | 0 349 869 | 1/1990 |
| GB | 2 089 810 | 6/1982 |
| SE | 314 978 | 9/1969 |
| SE | 330 883 | 12/1970 |
| SE | 430 508 | 11/1983 |
| WO | WO 96/00235 | 1/1996 |
| WO | WO 96/27658 | 9/1996 |

OTHER PUBLICATIONS

Alexander et al., "The Role of a 5.alpha.–Hydroxylated Intermediate in the Formation of the 5,6–Double Bond in Cholesterol Biosynthesis." Biochem. J., vol. 145, pp. 345–352, 1975.*
Anastasia et al., "Synthesis of 14.beta.–Cholesta–5, 7–Dien–3.beta.–ol." Steroids, vol. 49(6), pp. 543–552, 1987.*
Fieser et al., STEROIDS, pp. 925–945 (1967).
Byskov et al., Nature, vol. 374, pp. 559–562 (Apr. 6, 1995).
XP 002043016, Byskov et al., Nature, vol. 374, (Apr. 6, 1995.
Yoshida et al., Biochem. and Biophy. Res. Comm., vol. 223, pp. 534–538 (1996), Article No. 0929.
XP 002043016, Byskov et al., Nature, vol. 374, (Apr. 6, 1995).
Yoshida et al., Biochem. and Biophy. Res. Comm., vol. 223, pp. 534–538 (1996), Article No. 0929.

\* cited by examiner

*Primary Examiner*—Barbara P. Badio
(74) *Attorney, Agent, or Firm*—Len S. Smith; Reza Green

(57) ABSTRACT

Certain compounds, structurally related to natural compounds which can be extracted i.a. from bull testes and from human follicular fluid, can be used for regulating the meiosis in oocytes and in male germ cells. Some of these compounds are useful in the treatment of infertility, whereas other compounds are useful as contraceptives. These compounds have the structural formula

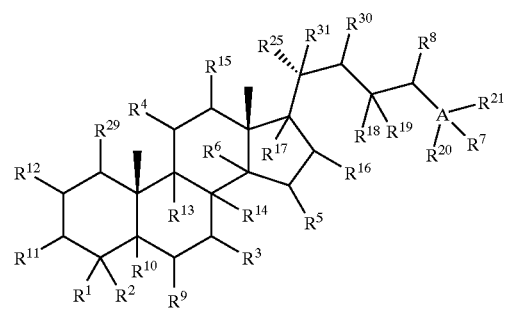

wherein the substituents are as defined in the specification.

6 Claims, No Drawings

US 6,759,400 B2

MEIOSIS REGULATING COMPOUNDS

CROSS-REFERENCE TO RELATED APPLICATIONS

This application is a continuation of U.S. application No. 09/764,203 filed on Jan. 17, 2001, now U.S. Pat. No. 6,486,145, which is a continuation of U.S. application Ser. No. 09/333,391 filed on Jun. 15, 1999, now abandoned which is a continuation of application no. PCT/DK97/00584 filed on Dec. 19,1997, and claims priority under 35 U.S.C. 119 of Danish application No. 1478/96 filed on Dec. 20, 1996, and U.S. provisional application No. 60/041,488 filed on Feb. 11, 1997, the contents of which are fully incorporated herein by reference.

FIELD OF THIS INVENTION

The present invention relates to pharmacologically active compounds and to their use as medicaments. More particularly it has been found that the sterol derivatives described herein can be used for regulating meiosis.

BACKGROUND OF THIS INVENTION

In L. F. Fieser & M. Fieser: Steroids; Reinhold Publishing Corporation, 1967, 5α-bromocholest-ane-3β,6β-diol; 7α-bromocholestane-3β,6α-diol; 7α-bromocholestane-3β,6β-diol; 7α-bromocholestane-3β,5α-diol-6-one; 7β-bromocholestane-3β,5α-diol-6-one; 3β-bromocholestane-2α-ol; 5α-chlorocholestane-3β,6α-diol; 5α-chlorocholestane-3β,6β-diol; 6β-chlorocholestane-3β,-5α-diol; $\Delta^{7,9(11)}$-cholestadiene-3β,6α-diol; $\Delta^{7,9(11)}$-cholestadiene-3β,6β-diol; cholestane-2α,3α-diol; cholestane-2α,3β-diol; cholestane-2β,3α-diol; cholestane-2β,3β-diol; cholestane-3α,4α-diol; cholestane-3α,4β-diol; cholestane-3β,4β-diol; cholestane-3α,5α-diol; cholestane-3β,5α-diol; cholestane-3β,6α-diol; cholestane-3β,6β-diol; cholestane-3β,22α-diol; cholestane-3β,22β-diol; cholestane-3β,7α,8α-triol; $\Delta^5$-cholestane-3β,4α-diol; $\Delta^5$-cholestane-3β,4β-diol; $\Delta^5$-cholestane-3β,22α-diol; $\Delta^5$-cholestane-3β,24β-diol; $\Delta^5$-cholestane-3β,22β-diol; $\Delta^5$-cholestane-3β,24α-diol; $\Delta^5$-cholestene-30,24β-diol; $\Delta^6$-cholestene-$\Delta^{8(14)}$-cholestene-3β,9α-diol; $\Delta^{11}$-cholestene-3α,24-diol; $\Delta^5$-cholestene-3β,6-diol-7-one; $\Delta^5$-cholestene-4α-ol-3-one; $\Delta^5$-cholestene-3β,4β,7α-triol; coprostane-3α,5β-diol; coprostane-3β,5β-diol; coprostane-3β,6β-diol; coprostane-4β,5β-diol-3-one and 20β-hydroxy-20-isocholesterol are mentioned in the subject index.

In German patent application having publication no. 1,183,079, a process for preparing 4α-hydroxy-5α-cholestan-3-one is mentioned in Example 5. This compound is not stated to have any utility other than as an intermediate.

In German patent application having publication no. 1,224,738, cholestan-3β,5α,6β-triol-3β-hemisuccinate; cholestan-3β,5α,6β-triol-3β-hemisuccinate-6β-acetate; cholestan-3β,5α,6β-triol-3β-hemisuccinate-6β-formiate; cholestan-3β,5α,6β-triol-3β-sulphate and cholestan-3β,5α,6β-triol-3β-phosphate are mentioned in Examples 1–5, respectively. It is mentioned that the compounds described therein can be used for the treatment of arteriosclerosis.

In German patent application having publication no. 2,201,991 C2, a process for the preparation of insecticides such as 2β,3β,14α,22(R),25-pentahydroxycholest-7-en-6-one is described.

German patent application having publication no. 2,236, 778 B2 relates to a novel insecticide, i.e., cholest-7-en-2β, 3β,5β,11β,14α,20(R),22(R)-heptahydroxy-6-one.

In German patent application having publication no. 2,409,971 B2, 5,24-cholestadien-3βol; 5-cholesten-3β,24, 25-triol-3β-acetate; 5-cholesten-3β,24,25-triol-3β,24-diacetate; 5,25-cholestadien-3β-ol acetate; 5-cholesten-3β, 25,26-triol-3β-acetate and 5-cholesten-3β,25,26-triol are mentioned in Examples 1, 1, 2, 3, 3 and 6, respectively. It is mentioned that the compounds described therein are valuable intermediates for the technical preparation of 24,25(or 25,26)-dihydroxycholecalciferol.

In German patent application having publication no. 2,453,648 B2, cholest-5α-an-3β,6α-diol; cholest-5β-an-3β, 6β-diol; cholest-5α-an-3,6-dione; cholest-5α-an-6β-ol-3-one and cholest-5α-an-2α-bromo-6β-ol-3-one are mentioned as intermediates in column 6.

In German patent application having publication no. 2,415,676, cholestan-30β,25-diol-3β-acetate; cholestan-3β, 5α,25-triol-3β-acetate; cholestan-3β,5α,25-triol; cholestan-5α,25-diol-3-one; cholest-4-en-25-ol-3-one and cholesta-4, 6-dien-25-ol-3-one are mentioned as compounds III, IV, X, XI XII and XIII, respectively. It is suggested that the compounds described therein may be substantially stronger that vitamin $D_3$.

In German patent application having publication no. 2,546,715 A1, a process for preparing 1α,3β-dihydroxycholest-5-en and 1α,3β-dihydroxycholest-6-en is mentioned in Example 1 (compounds V and II). It is suggested that the compounds described therein are useful additives to foodstuff and can be used in vitamin compositions.

In German patent application having publication no. 2,822,486 A1,3α,6α-dihydroxy-5β-cholestan-24-one; 3α,6α,24-trihydroxy-5β-cholestan; 3-chlorocholest-5,24-dien; 3β-hydroxycholest-5-en-24-on acetate and 3-chlorocholest-5-en-24-on are mentioned in Example 3, 4, 5a and 6c and as formula VII, respectively. It is mentioned that the compounds described therein can be used as intermediates for the preparation of desmosterin, derivatives thereof and other active vitamin D.

In German patent application having publication no. 3,241,172 A1, cholestan-25-fluoro-3β,22(S)-diol; cholestan-25-chloro-3β,22(S)-diol; cholestan-25-methyl-3β,22-diol; cholestan-25-methyl-3β,22-diol-3-hydrogenbutandioate and cholestan-25-methyl-3β,22-diol-bis-hydrogenbutandioate are mentioned in claims 2, 3, 5, 6 and 7, respectively. It is mentioned that the compounds described therein inhibit the activity of HMGCOA reductase and the formation of blood cholesterol.

In German patent application having publication no. 3,390,016 C2, a process for preparing 1α,25-dihydroxy-26, 26,26,27,27,27-hexafluorocholes-5-en is described. It is mentioned that this compound can easily be converted into a compound having vitamin $D_3$ like activity.

In Danish patent application having publication no. 123, 767, a process for preparing 2β,3β,14α,22,25-pentahydroxy-$\Delta^7$-5β-cholesten-6-one is mentioned. It is mentioned that the compounds described therein have an action on the central nervous system.

In European patent application having publication no. 15,122 B1, 25-hydroxy-3β-[(tetrahydro-2H-pyran-2-yl)oxy] cholest-5-en-24-on; 3β-[(tetrahydro-2H-pyran-2-yl)oxy] cholest-5-en-24-on; 25-hydroxy-24-oxocholesterol-3β-acetate; 24-oxocholesterol-3β-acetate; 25-hydroxy-24-oxocholesterol; 24,25-dihydroxycholesterol; 3α,6α,25-trihydroxy-24-oxo-5,β-cholestane; 1α,25-dihydroxy-24-oxocholesterol; 1α,24,25-trihydroxycholesterol; 3β-hydroxy-24-oxo-cholesta-5,7-dien; 3β,25-dihydroxy- 24-oxocholesta-5,7-dien; 3β-hydroxy-24-oxocholesta-5,7-dien; 1α,3β-dihydroxy-24-oxocholesta-5,7-dien and 1α,3β,25-trihydroxy-24-oxocholesta-5,7-dien are mentioned in Examples 1, 1, 4, 4, 5ii, 5(1), 6i, 7, 7(2), 8iii, 8iv, 8iv, 9iii and 9iv respectively. It is mentioned that the compounds described therein are useful intermediates convertible into active vitamin $D_3$.

In European patent application having publication ,no. 63,678 B1 (24R)-3β,24,25-trihydroxycholest-5-en; (24RS)-3β,24,25-trihydroxycholest-5-en and (24R)-1β,3β,24,25-tetrahydroxycholest-5-en are mentioned in Examples 1e, 3e and 4f, respectively. It is mentioned that the compounds described therein can be used as intermediates in the preparation of vitamin $D_3$ derivatives.

In European patent application having publication no. 322,036 A1, 4,4-dimethyl-24-methylene-3β-sulphooxy-12α-acetoxycholesta-8,14-dien-2α,11β-diol; 4,4-dimethyl-24-methylene-3β-sulphooxy-12α-acetoxycholest-8-en-2α,11β-diol; 4,4-dimethyl-24-methylene-12α-acetoxycholesta-8,14-dien-2α,3β,11β-triol; 4,4-dimethyl-24-methylene-12α-acetoxy-cholesta-8,14-dien-3β,11β-diol; 4,4-dimethyl-24-methylene-12α-acetoxycholest-8-en-2α,3β,11β-triol; 4,4-dimethyl-24-methylene-12α-acetoxycholest-8-en-3β,11β-diol; 4,4-dimethyl-24-methylenecholest-8-en-2,3β,11β,12α-tetraol; 4,4-dimethyl-24-methylene-3β-sulphooxycholesta-8,14-dien-2α,11β,12α-triol; 4,4-dimethyl-24-methylenecholesta-8,14-dien-2α,3β,11β,12α-tetraol; 4,4-dimethyl-24-methylene-3β-sulphooxy-12α-acetoxycholest-8-en-2-ol-11-one and mono(4,4-dimethyl-24-methylene-12α-acetoxycholesta-8,14-dien-2α,11β-diol)-3β-succinate are described in Tables I (1+2), II (5–9) and III (11–14). It is mentioned that the compounds described therein are anti-inflammatory.

In European patent application having publication no. 349,869 A2, 1α,3β-dihydroxycholest-5-ene and 1α,3β,24-trihydroxycholest-5-ene are mentioned in Examples 1 and 2, respectively. It is mentioned that the latter compound is useful for the production of 1α,24-dihydroxy-vitamin $D_3$.

In British patent application having publication no. 2,089,810 A, cholesta-5,7-diene-3β,23(R),25-triol and cholesta-5,7-diene-3β,23(S),25-triol are mentioned in Example 1. It is mentioned that the compounds described therein should find application as a substitute for 25-hydroxy vitamin $D_3$ in various therapeutic applications.

In Norwegian patent application having publication no. 144,264, 1α,3β-dihydroxycholest-5-en and 1α,3β,25-trihydroxycholest-5-en are mentioned in Example 1 and 3, respectively. It is mentioned that the compounds described therein can be used within the veterinary field.

In Swedish patent application having publication no. 314,978, a process wherein $\Delta^7$-cholesten-2β,3β-diol-6-one is used as starting material (for the preparation of $\Delta^7$-koprosten-2β,3β,14α-triol-6-one) is described in Example 3. The latter compound is active against insecticide metamorfose hormones.

In Swedish patent application having publication no. 330,883, 2β,3β,14α,22(R),25-pentahydroxy-$\Delta^7$-5,3cholesten-6-one and 2β,3β,14α,22(S),25-pentahydroxy-$\Delta^7$-5β-cholesten-6-one are mentioned in Examples 4 and 5, respectively. It is mentioned that the compounds described therein have valuable pharmacological properties; however, none is specified.

In Swedish patent application having publication no. 430,508, cholest-5-en-3β,22(R,S),25-triol; cholest-5-en-25-fluoro-3β,22(R,S)-diol; cholest-5-en-25-fluoro-22(R,S)-ol-3β-semisuccinate; cholest-5-en-25-chloro-3β,22-diol and cholest-5-en-25-chloro-22-ol-3β-hemisuccinate are mentioned in Examples 5, 8, 9, 11 and 12, respectively. It is mentioned that the compounds described therein have pharmaceutical activities, e.g., inhibiting (HMG-CoA) reductase.

In U.S. Pat. No. 3,931,403, 3α,7α,12α,24,25-pentahydroxy coprostane; 3α,7α,12α,25-tetrahydroxy coprostane; 3α,7α,25-trihydroxy coprostane; 3α,7α,24,25-tetrahydroxy coprostane; 5β-cholestane-3α,7α,12α,24α,25-pentol; 5β-cholestane-3α,7α,-12α,24β,25-pentol; 5β-cholestane-3α,7α,12α,25,26-pentol and 5β-cholestane-3α,7α,12α,25-tetrol are mentioned in Examples I and II. It is mentioned that the compounds described therein can be used to prepare a composition possessing antimicrobial, antibiotic and bacteriostatic properties.

In U.S. Pat. No. 4,011,250, 1α,2α,3β-trihydroxycholesta-5,7-diene and 1α,2β-dihydroxy-3β-acetoxycholesta-5-ene are described as intermediates in Example 1 and 3, respectively.

In U.S. Pat. No. 4,254,045, cholest-5-en-2β-fluoro-1α,3β-diol is mentioned as compound 3. It is mentioned that the compounds described therein have vitamin D-like activity.

In U.S. Pat. No. 4,329,295, the preparation of 24-cyclopropylchol-5-ene-3β,22(S)-diol-3-acatate, 24-cyclopropylchol-5-ene-3β,22(S)-diol, 24-cyclopropylchol-5-ene-3β,22(S)-diol 3 hydrogen butanedioate and 24-cyclopropyl-5α-cholane-3β,22(S)-diol is described in Examples 3–6, respectively. It is mentioned that the compounds described therein inhibit the activity of HMG Co A reductase.

In U.S. Pat. No. 4,670,190, cholesta-1,4,6-trien-3-one; 1α,3β-dihydroxycholest-5-ene; 1α,3β-dihydroxy-5α-cholestane; 1α,3β-dihydroxycholesta-5,7-diene; 1α,3β-25-trihydroxycholest-5-ene; 1α,25-dihydroxycholesterol; and 1α,25-dihydroxycholesterol-3-benzoate are described in Examples 1a, 1c, 2b', 3c, 4c, 9b and 9 c, respectively. It is mentioned that the compounds described therein have therapeutic applications.

Other known compounds are cholest-5-en-3β,20(S)-diol (Sigma, St. Louis, Mo., USA, Cat. No. H 6378), cholest-5-en-3β,22(S)-diol (Sigma, St. Louis, Mo., USA, Cat. No. H 5884), cholest-5-en-3β,4β-diol (Steraloid Inc., Wilton, N.H., USA, Cat. No. C 6410, Batch L 1066), cholest-5-en-3β,22 (R)-diol (Sigma, St. Louis, Mo., USA, Cat. No. H 9384) and 2β,3β,14α,22(R),25-pentahydroxycholest-7-en-6-one.

In none of the above publications is there any mentioning of the compounds being able to regulate meiosis. The content of the above publications is incorporated by reference.

Meiosis is the unique and ultimate event of germ cells on which sexual reproduction is based. Meiosis comprises two meiotic divisions. During the first division, exchange between maternal and paternal genes take place before the pairs of chromosomes are separated into the two daughter cells. These contain only half the number (1n) of chromosomes and 2c DNA. The second meiotic division proceeds without a DNA synthesis. This division therefore results in the formation of the haploid germ cells with only 1c DNA.

The meiotic events are similar in the male and female germ cells, but the time schedule and the differentiation processes which lead to ova and to spermatozoa differ profoundly. All female germ cells enter the prophase of the first meiotic division early in life, often before birth, but all are arrested as oocytes later in the prophase (dictyate state) until ovulation after puberty. Thus, from early life the female has a stock of oocytes which is drawn upon until the stock is exhausted. Meiosis in females is not completed until after fertilization, and results in only one ovum and two abortive polar bodies per germ cell. In contrast, only some of the male germ cells enter meiosis from puberty and leave a stem population of germ cells throughout life. Once initiated, meiosis in the male cell proceeds without significant delay and produces 4 spermatozoa.

Only little is known about the mechanisms which control the initiation of meiosis in the male and in the female. In the oocyte, new studies indicate that follicular purines, hypoxanthine or adenosine, could be responsible for meiotic arrest (Downs, S. M. et al. *Dev Biol* 82 (1985) 454–458; Eppig, J. J. et al. *Dev Biol* 119 (1986) 313–321; and Downs, S. M. *Mol Reprod Dev* 35 (1993) 82–94). The presence of a diffusible meiosis regulating substance was first described by Byskov et al. in a culture system of fetal mouse gonads (Byskov, A. G. et al. *Dev Biol* 52 (1976) 193–200). A meiosis activating substance (MAS) was secreted by the fetal mouse ovary in which meiosis was ongoing, and a meiosis preventing substance (MPS) was released from the morphologically differentiated testis with resting, non-meiotic germ cells. It was suggested that the relative concentrations of MAS and MPS regulated the beginning, arrest and resumption of meiosis in the male and in the female germ cells (Byskov, A. G. et al. in *The Physiology of Reproduction* (eds. Knobil, E. and Neill, J. D., Raven Press, New York (1994)). Clearly, if meiosis can be regulated, reproduction can be controlled. A recent article (Byskov, A. G. et al. *Nature* 374 (1995), 559–562) describes the isolation from bull testes and from human follicular fluid of certain sterols that activate oocyte meiosis. Unfortunately, these sterols are rather labile and utilization of the interesting finding would thus be greatly facilitated if more stable meiosis activating compounds were available.

Compounds being known to stimulate the meiosis and being different from the compounds claimed in the present patent application are described in WO 96/27658.

The compounds described herein have advantages compared with the known compounds.

SUMMARY OF THE INVENTION

It is a purpose of the present invention to provide compounds and methods useful for relieving infertility in females and males, particularly in mammals, more particularly in humans.

It is a further purpose of the present invention to provide compounds and methods useful as contraceptives in females and males, particularly in mammals, more particularly in humans.

According to the present invention there are provided novel compounds with interesting pharmacological properties. In particular, the compounds of formula Ia, Ib and Ic are useful for regulating the meiosis in oocytes and in male germ cells.

In one aspect, the present invention relates to compounds of formula Ia:

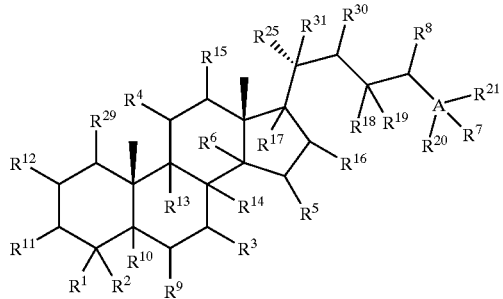

wherein $R^1$ and $R^2$, which are different or identical with the proviso that they are not both hydroxy, are selected from the group comprising hydrogen, halogen, hydroxy and branched or unbranched $C_1$–$C_5$ alkyl which may be substituted by halogen, hydroxy or cyano, or wherein $R^1$ and $R^2$ together designate methylene or oxo or, together with the carbon atom to which they are bound, form a cyclopropane ring, a cyclopentane ring, or a cyclohexane ring; $R^3$ is selected from the group comprising hydrogen, methylene, hydroxy, methoxy, acetoxy, oxo, halogen, $C_1$–$C_4$ alkandiyl (bound to the same carbon atom of the sterol skeleton) and $=NOR^{26}$ wherein $R^{26}$ is hydrogen or $C_1$–$C_3$ alkyl, or $R^3$ designates, together with $R^9$ or $R^{14}$, additional bond between the carbon atoms at which $R^3$ and $R^9$ or $R^{14}$ are placed; $R^4$ is selected from the group comprising hydrogen, methylene, hydroxy, methoxy, acetoxy, oxo, halogen, $C_1$–$C_4$ alkandiyl (bound to the same carbon atom of the sterol skeleton) and $=NOR^{27}$ wherein $R^{27}$ is hydrogen or $C_1$–$C_3$ alkyl, or $R^4$ designates, together with $R^{13}$ or $R^5$, an additional bond between the carbon atoms at which $R^4$ and $R^{13}$ or $R^{15}$ are placed; $R^{15}$ is Selected from the group comprising hydrogen, halogen, $C_1$–$C_4$ alkyl, methylene, hydroxy, methoxy, oxo and $=NOR^{22}$ wherein $R^{22}$ is hydrogen or $C_1$–$C_3$ alkyl, or $R^5$ designates, together with $R^8$ an additional bond between the carbon atoms at which $R^5$ and $R^6$ are placed; $R^6$ is hydrogen or hydroxy or $R^8$ designates, together with $R^5$, an additional bond between the carbon atoms at which $R^5$ and $R^6$ are placed; $R^9$ is hydrogen, hydroxy, halogen or oxo or $R^9$ designates, together with $R^3$ or $R^{10}$, an additional bond between the carbon atoms at which $R^9$ and $R^3$ or $R^{10}$ are placed; $R^{10}$ is hydrogen, halogen or hydroxy, or $R^{10}$ designates, together with $R^9$, an additional bond between the carbon atoms at which $R^{10}$ and $R^9$ are placed; $R^{11}$ is selected from the group comprising hydroxy, optionally substituted alkoxy, acyloxy, sulphonyloxy, phosphonyloxy, oxo, halogen, $C_1$–$C_4$ alkandiyl (bound to the same carbon atom of the sterol skeleton) and $=NOR^{28}$ wherein $R^{28}$ is hydrogen or $C_1$–$C_3$ alkyl, or $R^{11}$ designates, together with $R^{12}$, an additional bond between the carbon atoms at which $R^{11}$ and $R^{12}$ are placed; $R^{12}$ is selected from the group comprising hydrogen, hydroxy, $C_1$–$C_3$ alkyl, vinyl, $C_1$–$C_3$ alkoxy and halogen, or $R^{12}$ designates, together with $R^{11}$, an additional bond between the carbon atoms at which $R^{12}$ and $R^{11}$ are placed; $R^{13}$ is hydrogen, hydroxy or halogen or $R^{13}$ designates, together with $R^4$ or $R^{14}$, an additional bond between the carbon atoms at which $R^{13}$ and $R^4$ or $R^{14}$ are placed; $R^{14}$ is hydrogen, hydroxy or halogen, or $R^{14}$ designates, together with $R^3$, $R^6$ or $R_{13}$, an additional bond between the carbon atoms at which $R^{14}$ and $R^3$ or $R^6$ or $R^{13}$ are placed; $R^{15}$ is selected from the group comprising hydrogen, halogen, $C_1$–$C_4$ alkyl, methylene, hydroxy, methoxy, acetoxy, oxo and $=NOR^{23}$ wherein $R^{23}$ is hydrogen or $C_1$–$C_3$ alkyl, or $R^{15}$ designates, together with $R^4$, an additional bond between the carbon atoms at which $R^{15}$ and $R^4$ are placed; $R^{16}$ is selected from the group comprising hydrogen, halogen, $C_1$–$C_3$ alkyl, methylene, hydroxy, methoxy, oxo and $=NOR^{24}$ wherein $R^{24}$ is hydrogen or $C_1$–$C_3$ alkyl, or $R^{16}$ designates, together with $R^{17}$, an additional bond between the carbon atoms at which $R^{16}$ and $R^{17}$ are placed; $R^{17}$ is hydrogen or hydroxy, or $R^{17}$ designates, together with $R^{16}$, an additional bond between the carbon atoms at which $R^{17}$ and $R^{16}$ are placed; $R^{18}$ and $R^{19}$ are both hydrogen, or one of $R^{18}$ and $R^{19}$ is hydrogen while the other is halogen, hydroxy or methoxy, or $R^{18}$ and $R^{19}$ together designate oxo; $R^{25}$ is selected from the group comprising $C_1$–$C_4$ alkyl and hydroxymethyl, or $R^{25}$ and $R^{31}$ together designate methylene or oxo; $R^{29}$ is hydrogen, halogen, methyl, hydroxy or oxo; $R^{30}$ is hydrogen, halogen, methyl or hydroxy; $R^{31}$ is hydrogen, halogen, methyl or hydroxy, or $R^{31}$, together with $R^{25}$, designates methylene or oxo; and A is a carbon atom or a nitrogen atom; and when A is a carbon atom, $R^7$ is selected from the group comprising hydrogen, hydroxy and halogen; and $R^8$ is selected from the group comprising hydrogen, halogen, hydroxy, $C_1$–$C_4$ alkyl, methylene and oxo, or $R^7$ designates, together with $R^8$, an additional bond between the carbon atoms at which $R^7$ and $R^8$ are placed; $R^{20}$ is selected from the group comprising $C_1$–$C_4$ alkyl, trifluoromethyl and $C_3$–$C_6$ cycloalkyl, $R^{21}$ is selected from the group comprising $C_1$–$C_4$ alkyl, $C_1$–$C_4$ hydroxyalkyl, $C_1$–$C_4$ haloalkyl containing up to three halogen atoms, methoxymethyl, acetoxymethyl, and $C_3$–$C_6$ cycloalkyl, or $R^{20}$ and $R^{21}$, together with the carbon atom at which they are placed, form a $C_3$–$C_6$ cycloalkyl ring; and when A is a nitrogen atom, $R^7$ designates a lone pair of electrons; and $R^8$ is selected from the group comprising hydrogen, hydroxy, $C_1$–$C_4$ alkyl, cyano and oxo; and $R^{20}$ and $R^{21}$ are, independently, $C_1$–$C_4$ alkyl or $C_3$–$C_6$ cycloalkyl; with the general proviso that at least one of $R^1$, $R^2$, $R^6$, $R^8$, $R^9$, $R^{10}$, $R^{12}$, $R^{13}$, $R^{14}$, $R^{18}$, $R^{19}$, $R^{29}$, $R^{30}$ and $R^{31}$, is hydroxy or $R^{25}$ is hydroxymethyl and with the further general proviso that $R^9$, $R^{10}$ and $R^{11}$ are not all hydroxy and with the further general proviso that it is not 5α-bromocholestane-3β,6β-diol; 7α-bromo-cholestane-3β,6α-diol; 7α-bromocholestane -3β,6β-diol; 7α-bromocholestane-3β,5α-diol-6-one; 7β-bromocholestane-3β,5α-diol-6-one; 3β-bromocholestane-2α-ol; 5α-chlorocholestane-3β,6α-diol; 5α-chlorocholestane-3β,6β-diol; 6β-chlorocholestane-3β,5α-diol; $\Delta^{7,9(11)}$-cholestadiene-3β,-6α-diol; $\Delta^{7,9(11)}$-cholestadiene-3β,6β-diol; cholestane-2α,3α-diol; cholestane-2α,3β-diol; cholestane-2β,3α-diol; cholestane-2β,3β-diol; cholestane-3α,4α-diol; cholestane-3α,4β-diol; cholestane-3β,4β-diol; cholestane-3α,5α-diol; cholestane-3β,5α-diol; cholestane-3β,6α-diol; cholestane-3β,6β-diol; cholestane-3β,22α-diol; cholestane-3β,22β-diol; cholestane-3β,7α,8α-triol; $\Delta^5$-cholestene- 3β,4α-diol; $\Delta^5$-cholestene-3β,4β-diol; $\Delta^5$-cholestene-3β,20α-diol; $\Delta^5$-cholestone -3β,22α-diol; $\Delta^5$-cholestene-3β,22β-diol; $\Delta^5$-cholestene-3β,24α-diol; $\Delta^5$-cholestene-3β,24β-diol; $\Delta^6$-cholestene-3β,5α-diol; $\Delta^{8(14)}$-cholestene-3β,9α-diol-$\Delta^{11}$-cholestene-3α,24-diol; $\Delta^5$-cholestene-3β,6-diol-7-one; $\Delta^5$-cholestene-4α-ol-3-one; $\Delta^5$-cholestene-3β,4β7α-triol; coprostane-3α,5β-diol; coprostane-3β,5β-diol; coprostane-3β,6β-diol; coprostane-4β,5β-diol-3-one; 20β-hydroxy-20-isocholesterol; 4α-hydroxy-5α-cholestan-3-one; cholestan-3β,5α,6β-triol-3β-hemisuccinate; cholestan-3β,5α,6β-triol-3β-hemisuccinate-6β-acetate; cholestan-3β,5α,6β-triol-3β-hemisuccinate-6β-formiate; cholestan-3β,5α,6β-triol-3β-sulphate; cholestan-3β,5α,6β-triol-3β-hosphate; 2β,3β,14α,22(R),25-pentahydroxycholest-7-en-6-one; cholest-7-en-2β,3β,5β,11α,14α,20(R),22(R)-heptahydroxy-6-one; 5,24-cholestadien-3β-ol; 5-cholesten-3β,24,25-triol-3β-acetate; 5-cholesten-3β,24,25-triol-3β,24-diacetate; 5,25-cholestadien-3β-ol acetate; 5-cholesten-3β,25,26-triol-3β-acetate; 5-cholesten-3β,25,26-triol; 24,25(or 25,26)-dihydroxy-cholecalciferol; cholest-5α-an-3β,6α-diol; cholest-5β-an-3β,6β-diol; cholest-5α-an-3,6-dione; cholest-5α-an-6β-ol-3-one; cholest-5α-an-2α-bromo-6β-ol-3-one; cholestan-3β,25-diol-3β-acetate; cholestan-3β,5α,25-triol-3β-acetate; cholestan-3β,5α,25-triol; cholestan-5α,25-diol-3-one; cholest4-en-25-ol-3-one; cholesta-4,6-dien-25-ol-3-one; 1α,3β-dihydroxycholest-5-en; 1α,3β-dihydroxycholest-6-en; 3α,6α-dihydroxy-5β-cholestan-24-one; 3α,6α,24-trihydroxy-5β-cholestan; 3-chlorocholest-5,24-dien; 3β-hydroxycholest-5-en-24-on acetate; 3-chlorocholest-5-en-24-on; cholestan-25-fluoro-3β,22(S)-diol; cholestan-25-chloro-3β,22(S)-diol; cholestan-25-methyl-3β,22-diol; cholestan-25-methyl-3β,22-diol-3-hydrogenbutandioate; cholestan-25-methyl-3β,22-diol-bis-hydrogenbutandioate; 1α,25-dihydroxy-26,26,26,27,27,27-hexafluorocholes-5-en; 2β,3β,14α,22,25-pentahydroxy-$\Delta^7$-5β-cholesten-6-one; 25-hydroxy-3β-[(tetrahydro-2H-pyran-2-yl)oxy]cholest-5-en-24-on; 3β-[(tetrahydro-2H-pyran-2-yl)oxy]-cholest-5-en-24-on; 25-hydroxy-24-oxocholesterol-3β-acetate; 24-oxocholesterol-3β-acetate; 25-hydroxy-24-oxocholesterol; 24,25-dihydroxycholesterol; 3α,6α,25-trhydroxy-24-oxo-5β-cholestane; 1α,25-dihydroxy-24-oxocholesterol; 1α,24,25-trihydroxycholesterol; 3β-hydroxy-24-oxocholesta-5,7-dien; 3β,25-dihydroxy-24-oxocholesta-5,7-dien; 3β-hydroxy-24-oxo-cholesta-5,7-dien; 1α,3β-dihydroxy-24-oxocholesta-5,7-dien; 1α,3β,25-trihydroxy-24-oxo-cholesta-5,7-dien; (24R)-3β,24,25-trihydroxycholest-5-en; (24RS)-3β,24,25-trihydroxycholest-5-en; (24R)-1β,3β,24,25-tetrahydroxycholest-5-en; 4,4-dimethyl-24-methylene-3β-sulphooxy-12α-acetoxycholesta-8,14-dien-2α,11β-diol; 4,4-dimethyl-24-methylene-3β-sulphooxy-12α-acetoxycholest-8-en-2α,11β-diol; 4,4-dimethyl-24-methylene-12α-acetoxycholesta-8,14-dien-2α,3β,11β-triol; 4,4-dimethyl-24-methylene-12α-acetoxycholesta-8,14-dien-3β,11β-diol; 4,4-dimethyl-24-methylene-12α-acetoxycholest-8-en-2α,3β,11β-triol; 4,4-dimethyl-24-methylene-12α-acetoxycholest-8-en-3β,11β-diol; 4,4-dimethyl-24-methylenecholest-8-en-2,3β,11β,12α-tetraol; 4,4-dimethyl-24-methylene-3β-sulphooxycholesta-8,14-dien-2α,11β,12α-triol; 4,4-dimethyl-24-methylenecholesta-8,14-dien-2α,3β,11β,12α-tetraol; 4,4-dimethyl-24-methylene-3β-sulphooxy-12α-acetoxycholest-8-en-2-ol-11-one; mono(4,4-dimethyl-24-methylene-12α-acetoxycholesta-8,14-dien-2α,11β-diol)-3β-succinate; 1α,3β-dihydroxycholest-5-ene; 1α,3β,24-trihydroxycholest-5-ene; cholesta-5,7-diene-3β,23(R),25-triol; cholesta-5,7-diene-3β,23(S),25-triol; 1α,3β-dihydroxycholest-5-en; 1α,3β,25-trihydroxycholest-5-en; $\Delta^7$-cholesten-2β,3β-diol-6-one; 2β,3β14α,22(R),25-pentahydroxy-$\Delta^7$-5β-cholesten-6-one; 2β,3β,14α,22(S),25-pentahydroxy-$\Delta^7$-5β-cholesten-6-one; cholest-5-en-3β,22(R,S),25-triol; cholest-5-en-25-fluoro-3β,22(R,S)-diol; cholest-5-en-25-fluoro-22(R,S)-ol-3β-semisuccinate; cholest-5-en-25-chloro-3β,22-diol; cholest-5-en-25-chloro-22-ol-3β-hemisuccinate; 3α,7α,12α,24,25-pentahydroxy coprostane; 3α,7α,12α,25-tetrahydroxy coprostane; 3α,7α,25-trihydroxy coprostane; 3α,7α,24,25-tetrahydroxy coprostane; 5β-cholestane-3α,7α,12α,24α,25-pentol; 5β-cholestane-3α,7α,12α,24β,25-pentol; 5β-cholestane-3α,7α,12α,25,26-pentol; 5β-cholestane-3α,7α,12α,25-tetrol; 1α,2α,3β-trihydroxycholesta-5,7-diene; 1α,2α-dihydroxy-3β-acetoxycholesta-5-ene; cholest-5-en-2β-fluoro-1α,3α-diol; 24-cyclopropylchol-5-ene-3β,22(S)-diol-3-acatate,24-cyclopropylchol-5-ene-3β,22(S)-diol; 24-cyclopropylchol-5-ene-3β,22(S)-diol 3 hydrogen butanedioate; 24-cyclopropyl-5α-cholane-3β,22(S)-diol; cholesta-1,4,6-trien-3-one; 1α,3β-dihydroxycholest-5-ene; 1α,3β-dihydroxy-5α-cholestane; 1α,3β-dihydroxycholesta-5,7-diene; 1α,3β,25-trihydroxycholest-5-ene; 1α,25-dihydroxycholesterol; 1α,25-dihydroxycholesterol-3-benzoate; cholest-5-en-3β,20(S)-diol; 2β,3β,14α,22(R),25-pentahydroxycholest-7-en-6-one and cholest-5-en-3β,22(S)-diol; cholest-5-en-3β,20(S)-diol; cholest-5-en-3β,22(S)-diol; cholesta-5-en-3β,4β-diol; cholest-5-en-3β,22(R)-diol and 2β,3β,14α,22(R),25-pentahydroxy-cholest-7-en-6-one.

In another embodiment, the invention relates to esters of compound of formula Ia. Such esters are formally derived by esterification of one or more hydroxylic groups of a compound of formula Ia with an acid which, for example, can be selected from the group of acids comprising succinic acid and other aliphatic dicarboxylic acids, nicotinic acid, isonicotinic acid, ethylcarbonic acid, phosphoric acid, sulphonic acid, sulphamic acid, benzoic acid, acetic acid, propionic acid and other aliphatic monocarboxylic acids.

In still another preferred embodiment, the present invention relates to compounds of formula Ib and esters thereof as a medicament.

Compounds of formula Ib have the following structural formula:

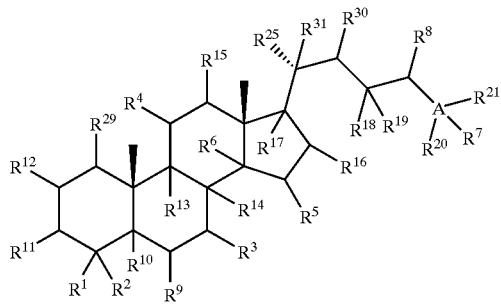

wherein $R^1$ and $R^2$, which are different or identical with the proviso that they are not both hydroxy, are selected from the group comprising hydrogen, halogen, hydroxy and branched or unbranched $C_1$–$C_6$ alkyl which may be substituted by halogen, hydroxy or cyano, or wherein $R^1$ and $R^2$ together designate methylene or oxo or, together with the carbon atom to which they are bound, form a cyclopropane ring, a cyclopentane ring, or a cyclohexane ring; $R^3$ is selected from the group comprising hydrogen, methylene, hydroxy, methoxy, acetoxy, oxo, halogen, $C_1$–$C_4$ alkandiyl (bound to the same carbon atom of the sterol skeleton) and =NO $R^{26}$ wherein $R^{26}$ is hydrogen or $C_1$–$C_3$ alkyl, or $R^3$ designates, together with $R^9$ or $R^{14}$, an additional bond between the carbon atoms at which $R^3$ and $R^9$ or $R^{14}$ are placed; $R^4$ is selected from the group comprising hydrogen, methylene, hydroxy, methoxy, acetoxy, oxo, halogen, $C_1$–$C_4$ alkandiyl (bound to the same carbon atom of the sterol skeleton) and =$NOR^{27}$ wherein $R^{27}$ is hydrogen or $C_1$–$C_3$ alkyl, or $R^4$ designates, together with $R^{13}$ or $R^{15}$, an additional bond between the carbon atoms at which $R^4$ and $R^{13}$ or $R^{15}$ are placed; $R^5$ is selected from the group comprising hydrogen, halogen, $C_1$–$C_4$ alkyl, methylene, hydroxy, methoxy, oxo and =$NOR^{22}$ wherein $R^{22}$ is hydrogen or $C_1$–$C_3$ alkyl, or $R^5$ designates, together with $R^6$ an additional bond between the carbon atoms at which $R^5$ and $R^6$ are placed; $R^6$ is hydrogen or hydroxy or $R^6$ designates, together with $R^5$, an additional bond between the carbon atoms at which $R^5$ and $R^5$ are placed; $R^9$ is hydrogen, hydroxy, halogen or oxo or $R^9$ designates, together with $R^3$ or $R^{10}$, an additional bond between the carbon atoms at which $R^9$ and $R^3$ or $R^{10}$ are placed; $R^{10}$ is hydrogen, halogen or hydroxy or $R^{10}$ designates, together with $R^9$, an additional bond between the carbon atoms at which $R^{10}$ and $R^9$ are placed; $R^{11}$ is selected from the group comprising hydroxy, optionally substituted alkoxy, acyloxy, sulphonyloxy, phosphonyloxy, oxo, halogen, $C_1$–$C_4$ alkandiyl (bound to the same carbon atom of the sterol skeleton) and =$NOR^{28}$ wherein $R^{28}$ is hydrogen or $C_1$–$C_3$ alkyl, or $R^{11}$ designates, together with $R^{12}$, an additional bond between the carbon atoms at which $R^{11}$ and $R^{12}$ are placed; $R^{12}$ is selected from the group comprising hydrogen, hydroxy, $C_1$–$C_3$ alkyl, vinyl, $C_1$–$C_3$ alkoxy and halogen, or $R^{12}$ designates, together with $R^{11}$, an additional bond between the carbon atoms at which $R^{12}$ and $R^{11}$ are placed; $R^{13}$ is hydrogen, hydroxy or halogen or $R^{13}$ designates, together with $R^4$ or $R^{14}$, an additional bond between the carbon atoms at which $R^{13}$ and $R^4$ or $R^{14}$ are placed; $R^{14}$ is hydrogen, hydroxy or halogen, or $R^{14}$ designates, together with $R^3$, $R^6$ or $R^{13}$, an additional bond between the carbon atoms at which $R^{14}$ and $R^3$ or $R^6$or $R^{13}$ are placed; $R^{15}$ is selected from the group comprising hydrogen, halogen, $C_1$–$C_4$ alkyl, methylene, hydroxy, methoxy, acetoxy, oxo and =$NOR^{23}$ wherein $R^{23}$ is hydrogen or $C_1$–$C_3$ alkyl, or $R^{15}$ designates, together with $R^4$, an additional bond between the carbon atoms at which $R^{15}$ and $R^4$ are placed; $R^{16}$ is selected from the group comprising hydrogen, halogen, $C_1$–$C_3$ alkyl, methylene, hydroxy, methoxy, oxo and =$NOR^{24}$ wherein $R^{24}$ is hydrogen or $C_1$–$C_3$ alkyl, or $R^{16}$ designates, together with $R^{17}$, an additional bond between the carbon atoms at which $R^{16}$ and $R^{17}$ are placed; $R^{17}$ is hydrogen or hydroxy, or $R^{17}$ designates, together with $R^{16}$, an additional bond between the carbon atoms at which $R^{17}$ and $R^{16}$ are placed; $R^{18}$ and $R^{19}$ are both hydrogen, or one of $R^{18}$ and $R^{19}$ is hydrogen while the other is halogen, hydroxy or methoxy, or $R^{18}$ and $R^{19}$ together designate oxo; $R^{25}$ is selected from the group comprising $C_1$–$C_4$ alkyl and hydroxymethyl, or $R^{25}$ and $R^{31}$ together designate methylene or oxo; $R^{29}$ is hydrogen, halogen, methyl, hydroxy or oxo; $R^{30}$ is hydrogen, halogen, methyl or hydroxy; $R^{31}$ is hydrogen, halogen, methyl or hydroxy, or $R^{31}$, together with $R^{25}$, designates methylene or oxo; and A is a carbon atom or a nitrogen atom; and when A is a carbon atom, $R^7$ is selected from the group comprising hydrogen, hydroxy and halogen; and $R^8$ is selected from the group comprising hydrogen, halogen hydroxy, $C_1$–$C_4$ alkyl, methylene and oxo, or $R^7$ designates, together with $R^8$, an additional bond between the carbon atoms at which $R^7$ and $R^8$ are placed; $R^{20}$ is selected from the group comprising $C_1$–$C_4$ alkyl, trifluoromethyl and $C_3$–$C_6$ cycloalkyl; $R^{21}$ is selected from the group comprising $C_1$–$C_4$ alkyl, $C_1$–$C_4$ hydroxyalkyl, $C_1$–$C_4$ haloalkyl containing up to three halogen atoms, methoxymethyl, acetoxymethyl, and $C_3$–$C_6$ cycloalkyl, or $R^{20}$ and $R^{21}$, together with the carbon atom at which they are placed, form a $C_3$–$C_6$ cycloalkyl ring; and when A is a nitrogen atom, $R^7$ designates a lone pair of electrons; and $R^8$ is selected from the group comprising hydrogen, hydroxy, $C_1$–$C_4$ alkyl, cyano and oxo; and $R^{20}$ and $R^{21}$ are, independently, $C_1$–$C_4$ alkyl or $C_3$–$C_6$ cycloalkyl; with the general proviso that at least one of $R^1$, $R^2$, $R^6$, $R^8$, $R^9$, $R^{10}$, $R^{12}$, $R^{13}$, $R^{14}$, $R^{18}$, $R^{19}$, $R^{29}$, $R^{30}$ and $R^{25}$ is hydroxymethyl, with the further general proviso that $R^9$, $R^{16}$ and $R^{11}$ are not all hydroxy, and with the further general proviso that it is not cholestan-3β,5α,6β-triol-3β-hemisuccinate; cholestan-3β,5α,6β-triol-3β-hemisuccinate-6β-acetate; cholestan-3β,5α,6β-triol-3β-hemisuccinate-6β-formiate; cholestan-3β,5α,6-triol-3β-sulphate; cholestan-3β,5α,6β-triol-3β-phosphate; cholestan-3β,25-diol-3β-acetate; cholestan-3β,5α,25-triol-3β-acetate; cholestan-3β,5α,25-triol; cholestan-5α,25-diol-3-one; cholest-4-en-25-ol-3-one; cholesta-4,6-dien-25-ol-3-one; 1α,3β-dihydroxycholest-5-en; 1α,3β-dihydroxycholest-6-en; 3α,6α-dihydroxy-5β-cholest-an-24-one; 3α,6α,24-trihydroxy-5β-cholestan; 3-chlorocholest-5,24-dien; 3β-hydroxycholest-5-en-24-on acetate; 3-chlorocholest-5-en-24-on; cholestan-25-fluoro-3β,22(S)-diol; cholestan-25-chloro-3β,22(S)-diol; cholestan-25-methyl-3β,22-diol; cholestan-25-methyl-3β,22-diol-3-hydrogenbutandioate; cholestan-25-methyl-3β,22-diol-bis-hydrogenbutandioate; 2β,3β,14α,-22,25-pentahydroxy-Δ$^7$-5β-cholesten-6-one; (24R)-3β,24,25-trihydroxycholest-5-en; (24RS)-3β,24,25- trihydroxycholest-5-en; (24R)-1β,3β,24,25-tetrahydroxycholest-5-en; 4,4-dimethyl-24-methylene-3β-sulphooxy-12α-acetoxycholesta-8,14-dien-2α,11β-diol; 4,4-dimethyl-24-methylene-3β-sulphooxy-12α-acetoxycholest-8-en-2α,11β-diol; 4,4-dimethyl-24-methylene-12α-acetoxycholesta-8,14-dien-2α,3β,11β-triol; 4,4-dimethyl-24-methylene-12α-acetoxy-cholesta-8,14-dien-3β,11β-diol; 4,4-dimethyl-24-methylene-12α-acetoxycholest-8-en-2α,3β,-11β-triol; 4,4-dimethyl-24-methylene-12α-acetoxycholest-8-en-3β,11β-diol; 4,4-dimethyl-24-methylenecholest-8-en-2,3β,11β,12α-tetraol; 4,4-dimethyl-24-methylene-3β-sulphooxy-cholesta-8,14-dien-2α,11β,12α-triol; 4,4-dimethyl-24-methylenecholesta-8,14-dien-2α,3β,-11β,12α-tetraol; 4,4-dimethyl-24-methylene-3β-sulphooxy-12α-acetoxycholest-8-en-2-ol-11-one; mono(4,4-dimethyl-24-methylene-12α-acetoxycholesta-8,14-dien-2α,11β-diol)-3β-succinate; cholesta-5,7-diene-3β,23(R),25-triol; cholesta-5,7-diene-3β,23(S),25-triol; 2β,3β,-14α,22(R),25-pentahydroxy-Δ⁷-5β-cholesten-6-one; 2β,3β,14α,22(S),25-pentahydroxy-Δ⁷-5β-cholesten-6-one; cholest-5-en-3β,22(R,S),25-triol; cholest-5-en-25-fluoro-3β,22(R,S)-diol; cholest-5-en-25-fluoro-22(R,S)-ol-3β-semisuccinate; cholest-5-en-25-chloro-3β,22-diol; cholest-5-en-25-chloro-22-ol-3β-hemisuccinate; 3α,7α,12α,24,25-pentahydroxy coprostane; 3α,7α,-12α,25-tetrahydroxy coprostane; 3α,7α,25-trihydroxy coprostane; 3α,7α,24,25-tetrahydroxy coprostane; 5β-cholestane-3α,7α,12α,24α,25-pentol; 5β-cholestane-3α,7α,12β,25-pentol; 5β-cholestane-3α,7α,12α,25,26-pentol; 5β-cholestane-3α,7α,12α,25-tetrol; cholest-5-2β-fluoro-1α,3β-diol; 24-cyclopropylchol-5-ene-3β,22(S)-diol-3-acatate, 24-cyclopropylchol-5-ene-3β,22(S)-diol, 24-cyclopropylchol-5-ene-3β,22(S)-diol 3 hydrogen butanedioate; 24-cyclo-propyl-5α-cholane-3β,22(S)-diol; cholesta-1,4,6-trien-3-one; 1α,3β-dihydroxycholest-5-ene; 1α,3β-dihydroxy-5α-cholestane; 1α,3β-dihydroxycholesta-5,7-diene; 1α,3β-25-trihydroxy-cholest-5-ene; 1α,25-dihydroxycholesterol; and 1α,25-dihydroxycholesterol-3-benzoate, as a medicament.

In a further preferred embodiment, this invention relates to compounds of formula Ic or esters thereof in the manufacture of a medicament for use in the regulation of meiosis.

Compounds of formula Ic have the following structural formula:

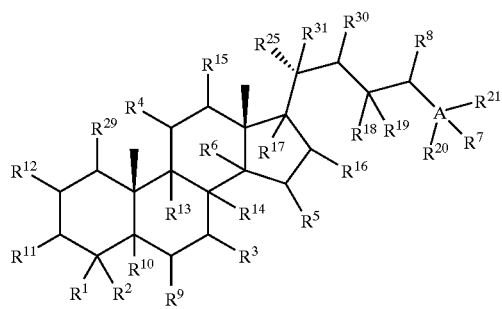

wherein $R^1$ and $R^2$, which are different or identical with the proviso that they are not both hydroxy are selected from the group comprising hydrogen, halogen, hydroxy and branched or unbranched $C_1-C_6$ alkyl which may be substituted by halogen, hydroxy or cyano, or wherein $R^1$ and $R^2$ together designate methylene or oxo or, together with the carbon atom to which they are bound, form a cyclopropane ring, a cyclopentane ring, or a cyclohexane ring; $R^3$ is selected from the group comprising hydrogen, methylene, hydroxy, methoxy, acetoxy, oxo, halogen, $C_1-C_4$ alkandiyl (bound to the same carbon atom of the sterol skeleton) and $=NOR^{26}$ wherein $R^{26}$ is hydrogen or $C_1-C_3$ alkyl, or $R^3$ designates, together with $R^9$ or $R^{14}$, an additional bond between the carbon atoms at which $R^3$ and $R^9$ or $R^{14}$ are placed; $R^4$ is selected from the group comprising hydrogen, methylene, hydroxy, methoxy, acetoxy, oxo, halogen, $C_1-C_4$ alkandiyl (bound to the same carbon atom of the sterol skeleton) and $=NOR^{27}$ wherein $R^{27}$ is hydrogen or $C_1-C_3$ alkyl, or $R^4$ designates, together with $R^{13}$ or $R^{15}$, an additional bond between the carbon atoms at which $R^4$ and $R^{13}$ or $R^{15}$ are placed; $R^5$ is selected from the group comprising hydrogen, halogen, $C_1-C_4$ alkyl, methylene, hydroxy, methoxy, oxo and $=NOR^{22}$ wherein $R^{22}$ is hydrogen or $C_1-C_3$ alkyl, or $R^5$ designates, together with $R^6$ an additional bond between the carbon atoms at which $R^5$ and $R^6$ are placed; $R^6$ is hydrogen or hydroxy or $R^6$ designates, together with $R^5$, an additional bond between the carbon atoms at which $R^5$ and $R^6$ are placed; $R^9$ is hydrogen, hydroxy, halogen or oxo or $R^9$ designates, together with $R^3$ or $R^{10}$, an additional bond between the carbon atoms at which $R^9$ and $R^3$ or $R^{10}$ are placed; $R^{10}$ is hydrogen, halogen or hydroxy, or $R^{10}$ designates, together with $R^9$, an additional bond between the carbon atoms at which $R^{10}$ and $R^9$ are placed; $R^{11}$ is selected from the group comprising hydroxy, optionally substituted alkoxy, acyloxy, sulphonyloxy, phosphonyloxy, oxo, halogen, $C_1-C_4$ alkandiyl (bound to the same carbon atom of the sterol skeleton) and $=NOR^{28}$ wherein $R^{28}$ is hydrogen or $C_1-C_3$ alkyl, or $R^{11}$ designates, together with $R^{12}$, an additional bond between the carbon atoms at which $R^{11}$ and $R^{12}$ are placed; $R^{12}$ is selected from the group comprising hydrogen, hydroxy, $C_1-C_3$ alkyl, vinyl, $C_1-C_3$ alkoxy and halogen, or $R^{12}$ designates, together with $R^{11}$, an additional bond between the carbon atoms at which $R^{12}$ and $R^{11}$ are placed; $R^{13}$ is hydrogen, hydroxy or halogen or $R^{13}$ designates, together with $R^4$ or $R^{14}$, an additional bond between the carbon atoms at which $R^{13}$ and $R^4$ or $R^{14}$ are placed; $R^{14}$ is hydrogen, hydroxy or halogen, or $R^{14}$ designates, together with $R^3$, $R^6$ or $R^{13}$, an additional bond between the carbon atoms at which $R^{14}$ and $R^3$ or $R^6$or $R^{13}$ are placed; $R^{15}$ is selected from the group comprising hydrogen, halogen, $C_1-C_4$ alkyl, methylene, hydroxy, methoxy, acetoxy, oxo and $=NOR^{23}$ wherein $R^{23}$ is hydrogen or $C_1-C_3$ alkyl, or $R^{15}$ designates, together with $R^4$, an additional bond between the carbon atoms at which $R^{15}$ and $R^4$ are placed; $R^{16}$ is selected from the group comprising hydrogen, halogen, $C_1-C_3$ alkyl, methylene, hydroxy, methoxy, oxo and $=NOR^{24}$ wherein $R^{24}$ is hydrogen or $C_1-C_3$ alkyl, or $R^{16}$ designates, together with $R^{17}$, an additional bond between the carbon atoms at which $R^{17}$ and $R^{17}$ are placed; $R^{17}$ is hydrogen or hydroxy, or $R^{17}$ designates, together with $R^6$, an additional bond between the carbon atoms at which $R^{17}$ and $R^{16}$ are placed; $R^{18}$ and $R^{19}$ are both hydrogen, or one of $R^{18}$ and $R^{19}$ is hydrogen while the other is halogen, hydroxy or methoxy, or $R^{18}$ and $R^{19}$ together designate oxo; $R^{25}$ is selected from the group comprising $C_1-C_4$ alkyl and hydroxymethyl, or $R^{25}$ and $R^{31}$ together designate methylene or oxo; $R^{29}$ is hydrogen, halogen, methyl, hydroxy or oxo; $R^{30}$ is hydrogen, halogen, methyl or hydroxy; $R^{31}$ is hydrogen, halogen, methyl or hydroxy, or $R^{31}$, together with $R^{25}$, designates methylene or oxo; and A is a carbon atom or a nitrogen atom; and when A is a carbon atom, $R^7$ is selected from the group comprising hydrogen, hydroxy and halogen; and $R^8$ is selected from the group comprising hydrogen, halogen, hydroxy, $C_1-C_4$ alkyl, methylene and oxo, or $R^7$ designates, together with $R^8$, an additional bond between the carbon atoms at which $R^7$ and $R^8$ are placed; $R^{20}$ is selected from the group comprising $C_1$–$C_4$ alkyl, trifluoromethyl and $C_3$–$C_6$ cycloalkyl; $R^{21}$ is selected from the group comprising $C_1$–$C_4$ alkyl, $C_1$–$C_4$ hydroxyalkyl, $C_1$–$C_4$ haloalkyl containing up to three halogen atoms, methoxymethyl, acetoxymethyl, and $C_3$–$C_6$ cycloalkyl, or $R^{20}$ and $R^{21}$, together with the carbon atom at which they are placed, form a $C_3$–$C_6$ cycloalkyl ring; and when A is a nitrogen atom, $R^7$ designates a lone pair of electrons; and $R^8$ is selected from the group comprising hydrogen, hydroxy, $C_1$–$C_4$ alkyl, cyano and oxo; and $R^{20}$ and $R^{21}$ are, independently, $C_1$–$C_4$ alkyl or $C_3$–$C_6$ cycloalkyl; with the general proviso that at least one of $R^1$, $R^2$, $R^6$, $R^8$, $R^9$, $R^{10}$, $R^{12}$, $R^{13}$, $R^{14}$, $R^{18}$, $R^{19}$, $R^{29}$, $R^{30}$ and $R^{31}$ is hydroxy or $R^{25}$ is hydroxymethyl, and with the further general proviso that $R^9$, $R^{10}$ and $R^{11}$ are not all hydroxy and with the further general proviso that it is not, for use in the regulation of meiosis.

In a further preferred aspect, the present invention relates to the use of a compound of formula Ic above or an ester thereof as a medicament, in particular as a medicament for use in the regulation of meiosis. The compound may be used neat or in the form of a liquid or solid composition containing auxiliary ingredients conventionally used in the art.

In the present context, the expression "regulating the meiosis" is used to indicate that certain of the compounds of the invention can be used for stimulating the meiosis in vitro, in vivo, or ex vivo. Thus, the compounds which may be agonists of a naturally occurring meiosis activating substance, can be used in the treatment of infertility which is due to insufficient stimulation of meiosis in females and in males. Other compounds of the invention, which may be antagonists of a naturally occurring meiosis activating substance, can be used for regulating the meiosis, preferably in vivo, in a way which makes them suited as contraceptives. In this case the "regulation" means partial or total inhibition.

In a still further preferred aspect, the present invention relates to the use of a compound of formula Ic above or an ester thereof in the regulation of the meiosis of an oocyte, in particular a mammalian oocyte, more particularly a human oocyte.

In a still further preferred aspect, the present invention relates to the use of a compound of formula Ic above or an ester thereof in the stimulation of the meiosis of an oocyte, in particular a mammalian oocyte, more particularly a human oocyte.

In a still further preferred aspect, the present invention relates to the use of a compound of formula Ic above or an ester thereof in the inhibition of the meiosis of an oocyte, in particular a mammalian oocyte, more particularly a human oocyte.

In a still further preferred aspect, the present invention relates to the use of a compound of formula Ic above or an ester thereof in the regulation of the meiosis of a male germ cell, in particular a mammalian male germ cell, more particularly a human male germ cell.

In a still further preferred aspect, the present invention relates to the use of a compound of formula Ic above or an ester thereof in the stimulation of the meiosis of a male germ cell, in particular a mammalian male germ cell, more particularly a human male germ cell.

In a still further preferred aspect, the present invention relates to the use of a compound of formula Ic above or an ester thereof in the inhibition of the meiosis of a male germ cell, in particular a mammalian male germ cell, more particularly a human male germ cell.

In a yet still further preferred aspect, the present invention relates to a method of regulating the meiosis in a mammalian germ cell which method comprises administering an effective amount of a compound of formula Ic above or an ester thereof to a germ cell in need of such a treatment.

In a still further aspect, the present invention relates to a method of regulating the meiosis in a mammalian germ cell wherein a compound of formula Ic above or an ester thereof is administered to the germ cell by administering the compound to a mammal hosting said cell.

In a still further aspect, the present invention relates to a method wherein the germ cell the meiosis of which is to be regulated by means of a compound of formula Ic above or an ester thereof is an oocyte.

In a still further aspect, the present invention relates to a method of regulating the meiosis in an oocyte wherein a compound of formula Ic above or an ester thereof is administered to the oocyte ex vivo.

In a still further aspect, the present invention relates to a method of regulating the meiosis of a male germ cell by administering a compound of formula Ic above or an ester thereof to the cell.

In a still further aspect, the present invention relates to a method whereby mature male germ cells are produced by administering in vivo or in vitro a compound of formula Ic above or an ester thereof to testicular tissue containing immature cells.

DETAILED DESCRIPTION OF THE INVENTION

Preferred compounds of formula Ia, Ib and Ic are such wherein $R^1$ and $R^2$ are both hydrogen.

Other preferred compounds of formula Ia, Ib and Ic are such wherein one of $R^1$ and $R^2$ is hydrogen while the other is methyl.

Other preferred compounds of formula Ia, Ib and Ic are such wherein $R^1$ and $R^2$ are both methyl.

Other preferred compounds of formula Ia, Ib and Ic are such wherein $R^1$ is branched or unbranched $C_1$–$C_6$ alkyl, optionally substituted by halogen, hydroxy or cyano.

Other preferred compounds of formula Ia, Ib and Ic are such wherein $R^2$ is branched or unbranched $C_1$–$C_6$ alkyl, optionally substituted by halogen, hydroxy or cyano.

Other preferred compounds of formula Ia, Ib and Ic are such wherein $R^1$ is hydroxy and $R^2$ is selected from the group comprising hydrogen and branched or unbranched $C_1$–$C_6$ alkyl which may be substituted by halogen, hydroxy or cyano.

Other preferred compounds of formula Ia, Ib and Ic are such wherein $R^2$ is hydroxy and $R^1$ is selected from the group comprising hydrogen and branched or unbranched $C_1$–$C_6$ alkyl which may be substituted by halogen, hydroxy or cyano.

Other preferred compounds of formula Ia, Ib and Ic are such wherein $R^1$ and $R^2$ together designate methylene.

Other preferred compounds of formula Ia, Ib and Ic are such wherein $R^1$ and $R^2$, together with the carbon atom to which they are bound, form a cyclopropane ring.

Other preferred compounds of formula Ia, Ib and Ic are such wherein $R^1$ and $R^2$, together with the carbon atom to which they are bound, form a cyclopentane ring.

Other preferred compounds of formula Ia, Ib and Ic are such wherein $R^1$ and $R^2$, together with the carbon atom to which they are bound, form a cyclohexane ring.

Other preferred compounds of formula Ia, Ib and Ic are such wherein $R^3$ is hydrogen.

Other preferred compounds of formula Ia, Ib and Ic are such wherein $R^3$ is methylene.

Other preferred compounds of formula Ia, Ib and Ic are such wherein $R^3$ is hydroxy.

Other preferred compounds of formula Ia, Ib and Ic are such wherein $R^3$ is methoxy or acetoxy.

Other preferred compounds of formula Ia, Ib and Ic are such wherein $R^3$ is halogen.

Other preferred compounds of formula Ia, Ib and Ic are such wherein $R^3$ is oxo.

Other preferred compounds of formula Ia, Ib and Ic are such wherein $R^3$ is =NOH.

Other preferred compounds of formula Ia, Ib and Ic are such wherein $R^3$ is =NOR$^{26}$, wherein $R^{26}$ is $C_1$–$C_3$ alkyl.

Other preferred compounds of formula Ia, Ib and Ic are such wherein $R^3$ is hydroxy and $C_1$–$C_4$ alkyl bound to the same carbon atom of the sterol skeleton.

Other preferred compounds of formula Ia, Ib and Ic are such wherein $R^3$, together with $R^9$, designates an additional bond between the carbon atoms at which $R^3$ and $R^9$ are placed.

Other preferred compounds of formula Ia, Ib and Ic are such wherein $R^3$, together with $R^{14}$, designates an additional bond between the carbon atoms at which $R^3$ and $R^{14}$ are placed.

Other preferred compounds of formula Ia, Ib and Ic are such wherein $R^4$ is hydrogen.

Other preferred compounds of formula Ia, Ib and Ic are such wherein $R^4$ is methylene.

Other preferred compounds of formula Ia, Ib and Ic are such wherein $R^4$ is hydroxy.

Other preferred compounds of formula Ia, Ib and Ic are such wherein $R^4$ is halogen.

Other preferred compounds of formula Ia, Ib and Ic are such wherein $R^4$ is methoxy or acetoxy.

Other preferred compounds of formula Ia, Ib and Ic are such wherein $R^4$ is oxo.

Other preferred compounds of formula Ia, Ib and Ic are such wherein $R^4$ is =NOH.

Other preferred compounds of formula Ia, Ib and Ic are such wherein $R^4$ is =NOR$^{27}$, wherein $R^{27}$ is $C_1$–$C_3$ alkyl.

Other preferred compounds of formula Ia, Ib and Ic are such wherein $R^4$ is hydroxy and $C_1$–$C_4$ alkyl bound to the same carbon atom of the sterol skeleton.

Other preferred compounds of formula Ia, Ib and Ic are such wherein $R^4$, together with $R^{13}$, designates an additional bond between the carbon atoms at which $R^4$ and $R^{13}$ are placed.

Other preferred compounds of formula Ia, Ib and Ic are such wherein $R^4$, together with $R^{15}$, designates an additional bond between the carbon atoms at which $R^4$ and $R^{15}$ are placed.

Other preferred compounds of formula Ia, Ib and Ic are such wherein $R^5$ is hydrogen.

Other preferred compounds of formula Ia, Ib and Ic are such wherein $R^5$ is halogen.

Other preferred compounds of formula Ia, Ib and Ic are such wherein $R^5$ is $C_1$–$C_4$ alkyl.

Other preferred compounds of formula Ia, Ib and Ic are such wherein $R^5$ is methylene.

Other preferred compounds of formula Ia, Ib and Ic are such wherein $R^5$ is hydroxy.

Other preferred compounds of formula Ia, Ib and Ic are such wherein $R^5$ is methoxy.

Other preferred compounds of formula Ia, Ib and Ic are such wherein $R^5$ is oxo.

Other preferred compounds of formula Ia, Ib and Ic are such wherein $R^5$ is =NOH.

Other preferred compounds of formula Ia, Ib and Ic are such wherein $R^5$ is =NOR$^{22}$, wherein $R^{22}$ is $C_1$–$C_3$ alkyl.

Other preferred compounds of formula Ia, Ib and Ic are such wherein $R^5$, together with $R^6$, designates an additional bond between the carbon atoms at which $R^5$ and $R^6$ are placed.

Other preferred compounds of formula Ia, Ib and Ic are such wherein $R^6$ is hydrogen.

Other preferred compounds of formula Ia, Ib and Ic are such wherein $R^6$ is hydroxy.

Other preferred compounds of formula Ia, Ib and Ic are such wherein $R^6$, together with $R^{14}$, designates an additional bond between the carbon atoms at which $R^5$ and $R^{14}$ are placed.

Other preferred compounds of formula Ia, Ib and Ic are such wherein $R^9$ is hydrogen.

Other preferred compounds of formula Ia, Ib and Ic are such wherein $R^9$ is halogen.

Other preferred compounds of formula Ia, Ib and Ic are such wherein $R^9$ is oxo.

Other preferred compounds of formula Ia, Ib and Ic are such wherein $R^9$ is hydroxy.

Other preferred compounds of formula Ia, Ib and Ic are such wherein $R^9$, together with $R^{10}$, designates an additional bond between the carbon atoms at which $R^9$ and $R^{10}$ are placed.

Other preferred compounds of formula Ia, Ib and Ic are such wherein $R^{10}$ is hydrogen.

Other preferred compounds of formula Ia, Ib and Ic are such wherein $R^{10}$ is halogen.

Other preferred compounds of formula Ia, Ib and Ic are such wherein $R^{10}$ is hydroxy.

Other preferred compounds of formula Ia, Ib and Ic are such wherein $R^{11}$ is hydroxy.

Other preferred compounds of formula Ia, Ib and Ic are such wherein $R^{11}$ is alkoxy, aralkyloxy, alkoxyalkoxy or alkanoyloxyalkyl, each group comprising a total of up to 10 carbon atoms, preferably up to 8 carbon atoms.

Other preferred compounds of formula Ia, Ib and Ic are such wherein $R^{11}$ is $C_1$–$C_4$ alkoxy.

Other preferred compounds of formula Ia, Ib and Ic are such wherein $R^{11}$ is methoxy.

Other preferred compounds of formula Ia, Ib and Ic are such wherein $R^{11}$ is ethoxy.

Other preferred compounds of formula Ia, Ib and Ic are such wherein $R^{11}$ is $CH_3OCH_2O$—.

Other preferred compounds of formula Ia, Ib and Ic are such wherein $R^{11}$ is pivaloyloxymethoxy.

Other preferred compounds of formula Ia, Ib and Ic are such wherein $R^{11}$ is an acyloxy group derived from an acid having from 1 to 20 carbon atoms.

Other preferred compounds of formula Ia, Ib and Ic are such wherein $R^{11}$ is an acyloxy group selected from the group comprising acetoxy, benzoyloxy, pivaloyloxy, butyryloxy, nicotinoyloxy, isonicotinoyloxy, hemi succinoyloxy, hemi glutaroyloxy, butylcarbamoyloxy, phenylcarbamoyloxy, butoxycarbonyloxy, tert-butoxycarbonyloxy and ethoxycarbonyloxy.

Other preferred compounds of formula Ia, Ib and Ic are such wherein $R^{11}$ is sulphonyloxy.

Other preferred compounds of formula Ia, Ib and Ic are such wherein $R^{11}$ is phosphonyloxy.

Other preferred compounds of formula Ia, Ib and Ic are such wherein $R^{11}$ is oxo.

Other preferred compounds of formula Ia, Ib and Ic are such wherein $R^{11}$ is =NOH.

Other preferred compounds of formula Ia, Ib and Ic are such wherein $R^{11}$ is =NOR$^{28}$, wherein $R^{28}$ is $C_1$–$C_3$ alkyl.

Other preferred compounds of formula Ia, Ib and Ic are such wherein $R^{11}$ is halogen.

Other preferred compounds of formula Ia, Ib and Ic are such wherein $R^{11}$ is hydroxy and $C_1$–$C_4$ alkyl bound to the same carbon atom of the sterol skeleton.

Other preferred compounds of formula Ia, Ib and Ic are such wherein $R^{11}$, together with $R^{12}$, designates an additional bond between the carbon atoms at which $R^{11}$ and $R^{12}$ are placed.

Other preferred compounds of formula Ia, Ib and Ic are such wherein $R^{12}$ is hydrogen.

Other preferred compounds of formula Ia, Ib and Ic are such wherein $R^{12}$ is hydroxy.

Other preferred compounds of formula Ia, Ib and Ic are such wherein $R^{12}$ is $C_1$–$C_3$ alkyl.

Other preferred compounds of formula Ia, Ib and Ic are such wherein $R^{12}$ is $C_1$–$C_3$ alkoxy.

Other preferred compounds of formula Ia, Ib and Ic are such wherein $R^{12}$ is halogen.

Other preferred compounds of formula Ia, Ib and Ic are such wherein $R^{13}$ is hydrogen.

Other preferred compounds of formula Ia, Ib and Ic are such wherein $R^{13}$ is halogen.

Other preferred compounds of formula Ia, Ib and Ic are such wherein $R^{13}$ is hydroxy.

Other preferred compounds of formula Ia, Ib and Ic are such wherein $R^3$, together with $R^{14}$, designates an additional bond between the carbon atoms at which $R^{13}$ and $R^{14}$ are placed.

Other preferred compounds of formula Ia, Ib and Ic are such wherein $R^{14}$ is hydrogen.

Other preferred compounds of formula Ia, Ib and Ic are such wherein $R^{14}$ is halogen.

Other preferred compounds of formula Ia, Ib and Ic are such wherein $R^{14}$ is hydroxy.

Other preferred compounds of formula Ia, Ib and Ic are such wherein $R^{15}$ is hydrogen.

Other preferred compounds of formula Ia, Ib and Ic are such wherein $R^{15}$ is halogen.

Other preferred compounds of formula Ia, Ib and Ic are such wherein $R^{15}$ is $C_1$–$C_4$ alkyl.

Other preferred compounds of formula Ia, Ib and Ic are such wherein $R^{15}$ is methylene.

Other preferred compounds of formula Ia, Ib and Ic are such wherein $R^{15}$ is hydroxy.

Other preferred compounds of formula Ia, Ib and Ic are such wherein $R^{15}$ is methoxy or acetoxy.

Other preferred compounds of formula Ia, Ib and Ic are such wherein $R^{15}$ is oxo.

Other preferred compounds of formula Ia, Ib and Ic are such wherein $R^{15}$ is =NOH.

Other preferred compounds of formula Ia, Ib and Ic are such wherein $R^{15}$ is =NOR$^{23}$, wherein $R^{23}$ is $C_1$–$C_3$ alkyl.

Other preferred compounds of formula Ia, Ib and Ic are such wherein $R^{16}$ is hydrogen.

Other preferred compounds of formula Ia, Ib and Ic are such wherein $R^{16}$ is halogen.

Other preferred compounds of formula Ia, Ib and Ic are such wherein $R^{16}$ is $C_1$–$C_3$ alkyl.

Other preferred compounds of formula Ia, Ib and Ic are such wherein $R^{16}$ is methylene.

Other preferred compounds of formula Ia, Ib and Ic are such wherein $R^{16}$ is hydroxy.

Other preferred compounds of formula Ia, Ib and Ic are such wherein $R^{16}$ is methoxy.

Other preferred compounds of formula Ia, Ib and Ic are such wherein $R^{16}$ is oxo.

Other preferred compounds of formula Ia, Ib and Ic are such wherein $R^{16}$ is =NOH.

Other preferred compounds of formula Ia, Ib and Ic are such wherein $R^{16}$ is =NOR$^{24}$, wherein $R^{24}$ is $C_1$–$C_3$ alkyl.

Other preferred compounds of formula Ia, Ib and IC are such wherein $R^{16}$ together with $R^{17}$, designates an additional bond between the carbon atoms at which $R^{16}$ and $R^{17}$ are placed.

Other preferred compounds of formula Ia, Ib and Ic are such wherein $R^{17}$ is hydrogen.

Other preferred compounds of formula Ia, Ib and Ic are such wherein $R^{17}$ is hydroxy.

Other preferred compounds of formula Ia, Ib and Ic are such wherein $R^{18}$ and $R^{19}$ are both hydrogen.

Other preferred compounds of formula Ia, Ib and Ic are such wherein one of $R^{18}$ and $R^{19}$ is hydrogen while the other is halogen.

Other preferred compounds of formula Ia, Ib and Ic are such wherein one of $R^{18}$ and $R^{19}$ is hydrogen while the other is hydroxy.

Other preferred compounds of formula Ia, Ib and Ic are such wherein one of $R^{18}$ and $R^{19}$ is hydrogen while the other is methoxy.

Other preferred compounds of formula Ia, Ib and Ic are such wherein one of $R^{18}$ and $R^{19}$ is fluoro and the other is hydrogen.

Other preferred compounds of formula Ia, Ib and Ic are such wherein $R^{18}$ and $R^{19}$ together designate oxo.

Other preferred compounds of formula Ia, Ib and Ic are such wherein $R^{25}$ is hydroxymethyl.

Other preferred compounds of formula Ia, Ib and Ic are such wherein $R^{25}$ is $C_1$–$C_4$ alkyl.

Other preferred compounds of formula Ia, Ib and Ic are such wherein $R^{25}$ together with $R^{31}$ designates methylene.

Other preferred compounds of formula Ia, Ib and Ic are such wherein $R^{25}$ together with $R^{31}$ designates oxo.

Other preferred compounds of formula Ia, Ib and Ic are such wherein $R^{29}$ is hydrogen.

Other preferred compounds of formula Ia, Ib and Ic are such wherein $R^{29}$ is halogen.

Other preferred compounds of formula Ia, Ib and Ic are such wherein $R^{29}$ is methyl.

Other preferred compounds of formula Ia, Ib and Ic are such wherein $R^{29}$ is hydroxy Other preferred compounds of formula Ia, Ib and Ic are such wherein $R^{29}$ is oxo.

Other preferred compounds of formula Ia, Ib and Ic are such wherein $R^{30}$ is hydrogen.

Other preferred compounds of formula Ia, Ib and Ic are such wherein $R^{30}$ is halogen.

Other preferred compounds of formula Ia, Ib and Ic are such wherein $R^{30}$ is methyl.

Other preferred compounds of formula Ia, Ib and Ic are such wherein $R^{30}$ is hydroxy.

Other preferred compounds of formula Ia, Ib and Ic are such wherein $R^{31}$ is hydrogen.

Other preferred compounds of formula Ia, Ib and Ic are such wherein $R^{31}$ is halogen.

Other preferred compounds of formula Ia, Ib and Ic are such wherein $R^{31}$ is methyl.

Other preferred compounds of formula Ia, Ib and Ic are such wherein $R^{31}$ is hydroxy Other preferred compounds of formula Ia, Ib and Ic are such wherein A is a carbon atom.

Other preferred compounds of formula Ia, Ib and Ic are such wherein A is a carbon atom, and $R^7$ is hydrogen.

Other preferred compounds of formula Ia, Ib and Ic are such wherein A is a carbon atom, and $R^7$ is hydroxy.

Other preferred compounds of formula Ia, Ib and Ic are such wherein A is a carbon atom, and $R^7$ is halogen.

Other preferred compounds of formula Ia, Ib and Ic are such wherein A is a carbon atom, and $R^7$, together with $R^8$, designates an additional bond between the carbon atoms at which $R^7$ and $R^8$ are placed.

Other preferred compounds of formula Ia, Ib and Ic are such wherein A is a carbon atom, and $R^8$ is hydrogen.

Other preferred compounds of formula Ia, Ib and Ic are such wherein A is a carbon atom, and $R^8$ is $C_1$–$C_4$ alkyl.

Other preferred compounds of formula Ia, Ib and Ic are such wherein A is a carbon atom, and $R^8$ is methylene.

Other preferred compounds of formula Ia, Ib and Ic are such wherein A is a carbon atom, and $R^8$ is oxo.

Other preferred compounds of formula Ia, Ib and Ic are such wherein A is a carbon atom, and $R^8$ is cyano.

Other preferred compounds of formula Ia, Ib and Ic are such wherein A is a carbon atom, and $R^8$ is halogen.

Other preferred compounds of formula Ia, Ib and Ic are such wherein A is a carbon atom, and $R^8$ is hydroxy.

Other preferred compounds of formula Ia, Ib and Ic are such wherein A is a carbon atom, and $R^{20}$ is $C_1$–$C_4$ alkyl.

Other preferred compounds of formula Ia, Ib and Ic are such wherein A is a carbon atom, and $R^{20}$ is trifluoromethyl.

Other preferred compounds of formula Ia, Ib and Ic are such wherein A is a carbon atom, and $R^{20}$ is $C_3$–$C_6$ cycloalkyl.

Other preferred compounds of formula Ia, Ib and Ic are such wherein A is a carbon atom, and $R^{21}$ is $C_1$–$C_4$ alkyl.

Other preferred compounds of formula Ia, Ib and Ic are such wherein A is a carbon atom, and $R^{21}$ is $C_1$–$C_4$ hydroxyalkyl.

Other preferred compounds of formula Ia, Ib and Ic are such wherein A is a carbon atom, and $R^{21}$ is $C_1$–$C_4$ haloalkyl containing up to three halogen atoms.

Other preferred compounds of formula Ia, Ib and Ic are such wherein A is a carbon atom, and $R^{21}$ is methoxymethyl or acetoxymethyl.

Other preferred compounds of formula Ia, Ib and Ic are such wherein A is a carbon atom, and $R^{21}$ is $C_3$–$C_6$ cycloalkyl.

Other preferred compounds of formula Ia, Ib and Ic are such wherein A is a carbon atom, and $R^{20}$ and $R^{21}$, together with the carbon atom to which they are bound, form a $C_3$–$C_6$ cycloalkyl ring, preferably a cyclopropyl ring, a cyclopentyl ring or a cyclohexyl ring.

Other preferred compounds of formula Ia, Ib and Ic are such wherein A is a nitrogen atom.

Other preferred compounds of formula Ia, Ib and Ic are such wherein A is a nitrogen atom, and $R^8$ is hydrogen.

Other preferred compounds of formula Ia, Ib and Ic are such wherein A is a nitrogen atom, and $R^8$ is hydroxy.

Other preferred compounds of formula Ia, Ib and Ic are such wherein A is a nitrogen atom, and $R^8$ is $C_1$–$C_4$ alkyl.

Other preferred compounds of formula Ia, Ib and Ic are such wherein A is a nitrogen atom, and $R^8$ is oxo.

Other preferred compounds of formula Ia, Ib and Ic are such wherein A is a nitrogen atom, and $R^{20}$ and $R^{21}$, independently, are selected from the group comprising $C_1$–$C_4$ alkyl, cyclopropyl, cyclopentyl and cyclohexyl.

Other preferred compounds of formula Ia, Ib and Ic are such wherein the long side chain in the 17 position is in the β position.

It is to be understood that the above preferred substituents can be combined in any way with each other.

Further preferred embodiments are recited in the appended claims.

As used in the present description and claims, the expression $C_1$–$C_3$ alkyl designates an alkyl group having from one to three carbon atoms; preferred examples are methyl, ethyl and propyl, more preferred methyl and ethyl. Similarly, the expression $C_1$–$C_4$ alkyl designates an alkyl group having from one to four carbon atoms; preferred examples are methyl, ethyl, propyl, isopropyl and butyl, more preferred methyl and ethyl. The expression $C_1$–$C_6$ alkyl designates an alkyl group having from one to six carbon atoms; preferred examples are methyl, ethyl, propyl, isopropyl, butyl, tert-butyl, pentyl and hexyl, more preferred methyl, ethyl, propyl, isopropyl, butyl and tert-butyl, still more preferred methyl and ethyl.

As used in the present description and claims, the expression $C_1$–$C_3$ alkoxy designates an alkoxy group having from one to three carbon atoms; preferred examples are methoxy, ethoxy and propoxy, more preferred methoxy and ethoxy.

As used in the present description and claims, the expression halogen preferably designates fluoro and chloro, more preferred fluoro.

As used in the present description and claims, the expression $C_1$–$C_4$ alkandiyl designates branched or unbranched alkane from which two hydrogen atoms have been removed. Looking at formula I, one can see that in these alkandiyl moieties the two free bonds are bound to the same carbon atom of the sterol skeleton. General terms for alkandiyl are believed to be alkylidene and alkylene. Examples of preferred alkandiyl moities are methylene, ethene, propylene, propylidene, isopropylidene, sec.butylidene and 1,4-butylene.

As used in the present description and claims, the expression $C_3$–$C_6$ cycloalkyl designates a cycloalkyl group containing 3–6 carbon atoms in the ring. Preferred examples are cyclopropyl and cyclopentyl.

As used in the present description and claims, the expression acyloxy designates a monovalent substituent comprising an optionally substituted $C_{1-6}$-alkyl or phenyl group linked through a carbonyloxy group; such as e.g. acetoxy, propionyloxy, butyryloxy, isobutyryloxy, pivaloyloxy, valeryloxy, benzoyl and the like.

The compounds of claim 1 have a number of chiral centers in the molecule and thus exist in several isomeric forms. All these isomeric forms and mixtures thereof are within the scope of the invention.

The compounds of formula I can be prepared analogously with the preparation of known compounds. Hence, synthesis of the compounds of formula I can follow the well established synthetic pathways described in the comprehensive sterol and steroid literature. The following books can be used as the key source in the synthesis: L. F. Fieser & M. Fieser: Steroids: Reinhold Publishing Corporation, NY 1959; Rood's Chemistry of Carbon Compounds (editor: S. Geoffrey): Elsevier Publishing Company, 1971; and especially Dictionary of Steriods (editors: R. A. Hill; D. N. Kirk; H. L. J. Makin and G. M. Murphy): Chapmann & Hall. The last one contains an extensive list of citations to the original papers covering the period up to 1990. All these books including the last mentioned citations are incorporated by reference.

The compounds of the present invention will influence the meiosis in oocytes as well as in male germ cells.

The existence of a meiosis inducing substance in nature has been known for some time. However, until recently the identity of the meiosis inducing substance or substances was unknown.

The prospects of being able to influence the meiosis are several. According to a preferred embodiment of the present invention, a compound of claim 1 or an ester thereof can be used to stimulate the meiosis. According to another preferred embodiment of the present invention, a compound of claim 1 or an ester thereof can be used to stimulate the meiosis in humans. Thus, the compounds of claim 1 and esters thereof are promising as new fertility regulating agents without the usual side effect on the somatic cells which are known from the hitherto used hormonal contraceptives which are based on estrogens and/or gestagens.

For use as a contraceptive agent in females, a meiosis inducing substance can be administered so as to prematurely induce resumption of meiosis in oocytes while they are still in the growing follicle, before the ovulatory peak of gonadotropins occurs. In women, the resumption of the meiosis can, for example, be induced a week after the preceding menstruation has ceased. When ovulated, the resulting overmature oocytes are then most likely not to be fertilized. The normal menstrual cycle is not likely to be affected. In this connection it is important to notice, that the biosynthesis of progesterone in cultured human granulosa cells (somatic cells of the follicle) is not affected by the presence of a meiosis inducing substance whereas the estrogens and gestagens used in the hitherto used hormonal contraceptives do have an adverse effect on the biosynthesis of progesterone.

According to another aspect of this invention, a meiosis inducing substance of formula 1a or an ester thereof can be used in the treatment of certain cases of infertility in females, including women, by administration thereof to females who, due to an insufficient own production of meiosis activating substance, are unable to produce mature oocytes. Also, when in vitro fertilization is performed, better results can be achieved, when a compound of formula 1a or an ester thereof is added to the medium in which the oocytes are kept.

When infertility in males, including men, is caused by an insufficient own production of the meiosis activating substance and thus a lack of mature sperm cells, administration of a compound of formula 1a or an ester thereof may relieve the problem.

As an alternative to the method described above, contraception in females can also be achieved by administration of a compound of formula 1 a or an ester thereof which inhibits the meiosis, so that no mature oocytes are produced. Similarly, contraception in males can be achieved by administration of a compound of formula 1a or an ester thereof which inhibits the meiosis, so that no mature sperm cells are produced.

The route of administration of compositions containing a compound of formula 1a or an ester thereof may be any route which effectively transports the active compound to its site of action.

Thus, when the compounds of this invention are to be administered to a mammal, they are conveniently provided in the form of a pharmaceutical composition which comprises at least one compound of formula 1a or an ester thereof in connection with a pharmaceutically acceptable carrier. For oral use, such compositions are preferably in the form of capsules or tablets.

From the above it will be understood that administrative regimen called for will depend on the condition to be treated. Thus, when used in the treatment of infertility the administration may have to take place once only, or for a limited period, e.g. until pregnancy is achieved. When used as a contraceptive, the compound of formula 1a or an ester thereof will either have to be administered continuously or cyclically. When used as a contraceptive by females and not taken continuously, the timing of the administration relative to the ovulation will be important.

Examples of preferred compounds according to the invention are given below:
cholesta-5-en-3α,1β-diol; cholesta-5-en-3α,1α-diol; cholesta-5-en-3α,2β-diol; cholesta-5-en-3α,2α-diol; cholesta-5-en-3α,4β-diol; cholesta-5-en-3α,4α-diol; cholesta-5-en-3α,7β-diol; cholesta-5-en-3α,7α-diol; cholesta-5-en-3α,11β-diol; cholesta-5-en-3α,11α-diol; cholesta-5-en-3α,12β-diol; cholesta-5-en-3α,12α-diol; cholesta-5-en-3α,15β-diol; cholesta-5-en-3α15α-diol; cholesta-5-en-3α,16β-diol; cholesta-5-en-3α,16α-diol; cholesta-5-en-3α,17β-diol; cholesta-5-en-3α,17α-diol; cholesta-5-en-3α,(20R)-diol; cholesta-5-en-3α,(20S)-diol; cholesta-5-en-3α,21-diol; cholesta-5-en-3α,(22R)-diol; cholesta-5-en-3α,(22S)-diol; cholesta-5-en-3α,(23R)-diol; cholesta-5-en-3α,(23S)-diol; cholesta-5-en-3α,(24R)-diol; cholesta-5-en-3α,(24S)-diol; cholesta-5-en-3α,25-diol; (25R)-cholesta-5-en-3α,26-diol; (25S)-cholesta-5-en-3α,26-diol; cholesta-5-en-3β,1β-diol; cholesta-5-en-3β,1α-diol; cholesta-5-en-3β,2β-diol; cholesta-5-en-3β,2α-diol; cholesta-5-en-3β,4β-diol; cholesta-5-en-3β,4α-diol; cholesta-5-en-3β,7β-diol; cholesta-5-en-3β,7α-diol; cholesta-5-en-3β,11β-diol; cholesta-5-en-3β,11α-diol; cholesta-5-en-3β,12β-diol; cholesta-5-en-3β,12α-diol; cholesta-5-en-3β,15β-diol; cholesta-5-en-3β,15α-diol; cholesta-5-en-3β,16β-diol; cholesta-5-en-3β,16α-diol; cholesta-5-en-3β,17β-diol; cholesta-5-en-3β,17α-diol; cholesta-5-en-3β,(20R)-diol; cholesta-5-en-3β,(20S)-diol; cholesta-5-en-3β,21-diol; cholesta-5-en-3β,(22S)-diol; cholesta-5-en-3β,(23R)-diol; cholesta-5-en-3β,(23S)-diol; cholesta-5-en-3β,(24R)-diol; cholesta-5-en-3β,(24S)-diol; cholesta-5-en-3β,25-diol; (25S)-cholesta-5-en-3β,26-diol; cholesta-5,24-dien-3α,1β-diol; cholesta-5,24-dien-3α,1α-diol; cholesta-5,24-dien-3α,2β-diol; cholesta-5,24-dien-3α,2α-cholesta-5,24-dien-3α,4β-diol; cholesta-5,24-dien-3α,4α-diol; cholesta-5,24-dien-3α,7β-diol; cholesta-5,24-dien-3α,7α-diol; cholesta-5,24-dien-3α,11β-diol; cholesta-5,24-dien-3α,11α-diol; cholesta-5,24-dien-3α,12β-diol; cholesta-5,24-dien-3α,12α-diol; cholesta-5,24-dien-3α,15β-diol; cholesta-5,24-dien-3α,15α-diol;

cholesta-5,24-dien-3α,16β-diol; cholesta-5,24-dien-3α,16α-diol; cholesta-5,24-dien-3α,17β-diol; cholesta-5,24-dien-3α,17α-diol; cholesta-5,24-dien-3α,(20R)-diol; cholesta-5,24-dien-3α,(20S)-diol; cholesta-5,24-dien-3α,21-diol; cholesta-5,24-dien-3α,(22R)-diol; cholesta-5,24-dien-3α,(22S)-diol; cholesta-5,24-dien-3α,(23R)-diol; cholesta-5,24-dien-3α,(23S)-diol; cholesta-5,24-dien-3α,26-diol; cholesta-5,24-dien-3β,1β-diol; cholesta-5,24-dien-3β,1α-diol; cholesta-5,24-dien-3β,2β-diol; cholesta-5,24-dien-3β,2α-diol; cholesta-5,24-dien-3β,4β-diol; cholesta-5,24-dien-3β,4α-diol; cholesta-5,24-dien-3β,7β-diol; cholesta-5,24-dien-3β,7α-diol; cholesta-5,24-dien-3β,11β-diol; cholesta-5,24-dien-3β,11α-diol; cholesta-5,24-dien-3β,12β-diol; cholesta-5,24-dien-3β,12α-diol; cholesta-5,24-dien-3β,15β-diol; cholesta-5,24-dien-3β,15α-diol; cholesta-5,24-dien-3β,16β-diol; cholesta-5,24-dien-3β,16α-diol; cholesta-5,24-dien-3β,17β-diol; cholesta-5,24-dien-3β,17α-diol; cholesta-5,24-dien-3β,(20R)-diol; cholesta-5,24-dien-3β,(20S)-diol; cholesta-5,24-dien-3β,21-diol; cholesta-5,24-dien-3β,(22R)-diol; cholesta-5,24-dien-3β,(22S)-diol; cholesta-5,24-dien-3β,(23R)-diol; cholesta-5,24-dien-3β,(23S)-diol; cholesta-5,24-dien-3β,26-diol; 4,4-dimethylcholesta-5-en-3α,1β-diol; 4,4-dimethylcholesta-5-en-3α,1α-diol; 4,4-dimethylcholesta-5-en-3α,2β-diol; 4,4-dimethylcholesta-5-en-3α,2α-diol; 4,4-dimethylcholesta-5-en-3α,7β-diol; 4,4-dimethylcholesta-5-en-3α,7α-diol; 4,4-dimethylcholesta-5-en-3α,11β-diol; 4,4-dimethylcholesta-5-en-3α,11α-diol; 4,4-dimethylcholesta-5-en-3α,12β-diol; 4,4-dimethylcholesta-5-en-3α,12α-diol; 4,4-dimethylcholesta-5-en-3α,15,β-diol; 4,4-dimethylcholesta-5-en-3α15α-diol; 4,4-dimethylcholesta-5-en-3α,16β-diol; 4,4-dimethylcholesta-5-en-3α,16α-diol; 4,4-dimethylcholesta-5-en-3α,17β-diol; 4,4-dimethylcholesta-5-en-3α,17α-diol; 4,4-dimethylcholesta-5-en-3α,(20R)-diol; 4,4-dimethylcholesta-5-en-3α,(20S)-diol; 4,4-dimethylcholesta-5-en-3α,21-diol; 4,4-dimethylcholesta-5-en-3α,(22R)-diol; 4,4-dimethylcholesta-5-en-3α,(22S)-diol; 4,4-dimethylcholesta-5-en-3α,(23R)-diol; 4,4-dimethylcholesta-5-en-3α,(23S)-diol; 4,4-dimethylcholesta-5-en-3α,(24R)-diol; 4,4-dimethylcholesta-5-en-3α,(24S)-diol; 4,4-dimethylcholesta-5-en-3α,25-diol; (25R)-4,4-dimethylcholesta-5-en-3α,26-diol; (25S)-4,4-dimethylcholesta-5-en-3α,26-diol; 4,4-dimethylcholesta-5-en-3β,1β-diol; 4,4-dimethylcholesta-5-en-3β,1α-diol; 4,4-dimethylcholesta-5-en-3β,2β-diol; 4,4-dimethylcholesta-5-en-3β,2α-diol; 4,4-dimethylcholesta-5-en-3β,7β-diol; 4,4-dimethylcholesta-5-en-3β,7α-diol; 4,4-dimethylcholesta-5-en-3β,11β-diol; 4,4-dimethylcholesta-5-en-3β,11α-diol; 4,4-dimethylcholesta-5-en-3β,12β-diol; 4,4-dimethylcholesta-5-en-3β,12α-diol; 4,4-dimethylcholesta-5-en-3β,15β-diol; 4,4-dimethylcholesta-5-en-3β,15α-diol; 4,4-dimethylcholesta-5-en-3β,16β-diol; 4,4-dimethylcholesta-5-en-3β,16α-diol; 4,4-dimethylcholesta-5-en-3β,17β-diol; 4,4-dimethylcholesta-5-en-3β,17α-diol; 4,4-dimethylcholesta-5-en-3β,(20R)-diol; 4,4-dimethylcholesta-5-en-3β,(20S)-diol; 4,4-dimethylcholesta-5-en-3β,21-diol; 4,4-dimethylchalesta-5-en-3β,(22R)-diol; 4,4-dimethylcholesta-5-en-3β,(22S)-diol; 4,4-dimethylcholesta-5-en-3β,(23R)-diol; 4,4-dimethylcholesta-5-en-3β,(23S)-diol; 4,4-dimethylcholesta-5-en-3β,(24R)-diol; 4,4-dimethylcholesta-5-en-3β,(24S)-diol; 4,4-dimethylcholesta-5-en-3β,25-diol; (25R)-4,4-dimethylcholesta-5-en-3β,26-diol; (25S)-4,4-dimethylcholesta-5-en-3β,26-diol; 4,4-dimethylcholesta-5,24-dien-3α,1β-diol; 4,4-dimethylcholesta-5,24-dien-3α,1α-diol; 4,4-dimethylcholesta-5,24-dien-3α,2β-diol; 4,4-dimethylcholesta-5,24-dien-3α,2α-diol; 4,4-dimethylcholesta-5,24-dien-3α,7β-diol; 4,4-dimethylcholesta-5,24-dien-3α,7α-diol; 4,4-dimethylcholesta-5,24-dien-3α,11β-diol; 4,4-dimethylcholesta-5,24-dien-3α,11α-diol; 4,4-dimethylcholesta-5,24-dien-3α,12β-diol; 4,4-dimethylcholesta-5,24-dien-3α,12α-diol; 4,4-dimethylcholesta-5,24-dien-3α,15β-diol; 4,4-dimethylcholesta-5,24-dien-3α,15α-diol; 4,4-dimethylcholesta-5,24-dien-3α,16β-diol; 4,4-dimethylcholesta-5,24-dien-3α,16α-diol; 4,4-dimethylcholesta-5,24-dien-3α,17β-diol; 4,4-dimethylcholesta-5,24-dien-3α,17α-diol; 4,4-dimethylcholesta-5,24-dien-3α,(20R)-diol; 4,4-dimethylcholesta-5,24-dien-3α,(20S)-diol; 4,4-dimethylcholesta-5,24-dien-3α,21-diol; 4,4-dimethylcholesta-5,24-dien-3α,(22R)-diol; 4,4-dimethylcholesta-5,24-dien-3α,(22S)-diol; 4,4-dimethylcholesta-5,24-dien-3α,(23R)-diol; 4,4-dimethylcholesta-5,24-dien-3α,(23S)-diol; 4,4-dimethylcholesta-5,24-dien-3α,26-diol; 4,4-dimethylcholesta-5,24-dien-3β,1β-diol; 4,4-dimethylcholesta-5,24-dien-3β,1α-diol; 4,4-dimethytcholesta-5,24-dien-3β,2β-diol; 4,4-dimethylcholesta-5,24-dien-3β,2α-diol; 4,4-dimethylcholesta-5,24-dien-3β,7β-diol; 4,4-dimethylcholesta-5,24-dien-3β,7α-diol; 4,4-dimethylcholesta-5,24-dien-3β,11β-diol; 4,4-dimethylcholesta-5,24-dien-3β,11α-diol; 4,4-dimethylcholesta-5,24-dien-3β,12β-diol; 4,4-dimethylcholesta-5,24-dien-3β,12α-diol; 4,4-dimethylcholesta-5,24-dien-3β,15β-diol; 4,4-dimethylcholesta-5,24-dien-3β,15α-diol; 4,4-dimethylcholesta-5,24-dien-3β,16β-diol; 4,4-dimethylcholesta-5,24-dien-3β,16α-diol; 4,4-dimethylcholesta-5,24-dien-3β,17β-diol; 4,4-dimethylcholesta-5,24-dien-3β,17α-diol; 4,4-dimethylcholesta-5,24-dien-3β,(20R)-diol; 4,4-dimethylcholesta-5,24-dien-3β,(20S)-diol; 4,4-dimethylcholesta-5,24-dien-3β,21-diol; 4,4-dimethylcholesta-5,24-dien-3β,(22R)-diol; 4,4-dimethylcholesta-5,24-dien-3β,(22S)-diol; 4,4-dimethylcholesta-5,24-dien-3β,(23R)-diol; 4,4-dimethylcholesta-5,24-dien-3β,(23S)-diol; 4,4-dimethylcholesta-5,24-dien-3β,26-diol; spiro[cholesta-5-en-3α,7β-diol-4,1'-cyclopropane]; spiro[cholesta-5-en-3α,7α-diol-4,1'-cyclopropane]; spiro[cholesta-5-en-3α,11β-diol-4,1'-cyclopropane]; spiro[cholesta-5-en-3α,11α-diol-4,1'-cyclopropane]; spiro[cholesta-5-en-3α,12β-diol-4,1'-cyclopropane]; spiro[cholesta-5-en-3α,12α-diol-4,1'-cyclopropane]; spiro[cholesta-5-en-3α,15β-diol-4,1'-cyclopropane]; spiro[cholesta-5-en-3α,15α-diol-4,1'-cyclopropane]; spiro[cholesta-5-en-3α,16β-diol-4,1'-cyclopropane]; spiro[cholesta-5-en-3α,16α-diol-4,1'-cyclopropane]; spiro[cholesta-5-en-3α,17β-diol-4,1'-cyclopropane]; spiro[cholesta-5-en-3α,17α-diol-4,1'-cyclopropane]; spiro[cholesta-5-en-3α,(20R)-diol-4,1'-cyclopropane]; spiro[cholesta-5-en-3α,(20S)-diol-4,1 '-cyclopropane]; spiro[cholesta-5-en-3α, 21-diol-4,1'-cyclopropane]; spiro[cholesta-5-en-3α,(22R)-diol-4,1'-cyclopropane]; spiro[cholesta-5-en-3α,(22S)-diol-4,1'-cyclopropane]; spiro[cholesta-5-en-3α,(23R)-diol-4,1'-cyclopropane]; spiro[cholesta-5-en-3α,(23S)-diol-4,1'-cyclopropane]; spiro[cholesta-5-en-3α,(24R)-diol-4,1'-cyclopropane]; spiro[cholesta-5-en-3α,(24S)-diol-4,1'-cyclopropane]; spiro[cholesta-5-en-3α,25-diol-4,1'-cyclopropane]; spiro[(25R)-cholesta-5-en-3α,26-diol-4,1'-cyclopropane]; spiro[(25S)-cholesta-5-en-3α,26-diol-4,1'-cyclopropane]; spiro[cholesta-5-en-3β,7β-diol-4,1'-cyclopropane]; spiro[cholesta-5-en-3β,7α-diol-4,1'-cyclolpropane]; spiro[cholesta-5-en-3β,11β-diol-4,1'-cyclopropane]; spiro[cholesta-5-en-3β,11α-diol-4,1'-cyclopropane]; spiro[cholesta-5-en-3β,12β-diol-4,1'-cyclopropane]; spiro[cholesta-5-en-3β,12α-diol-4,1'-cyclopropane]; spiro[cholesta-5-en-3β,15β-diol-4,1'-cyclopropane]; spiro[cholesta-5-en-3β,15α-diol-4,1'-cyclopropane]; spiro[cholesta-5-en-3β,16β-diol-4,1'-cyclopropane]; spiro[cholesta-5-en-3β,16α-diol-4,1'-cyclopropane]; spiro[cholesta-5-en-3β,17β-diol-4,1'-cyclopropane]; spiro[cholesta-5-en-3β,17α-diol-4,1'-cyclopropane]; spiro[cholesta-5-en-3β,(20R)-diol-4,1'-cyclopropane]; spiro[cholesta-5-en-3β,(20S)-diol-4,1'-cyclopropane]; spiro[cholesta-5-en-3β,21-diol-4,1'-cyclopropane]; spiro[cholesta-5-en-3β,(22R)-diol-4,1'-cyclopropane]; spiro[cholesta-5-en-3β,(22S)-diol-4,1'-cyclopropane]; spiro[cholesta-5-en-3β,(23R)-diol-4,1'-cyclopropane]; spiro[cholesta-5-en-3β,(23S)-diol-4,1'-cyclopropane]; spiro[cholesta-5-en-3β,(24R)-diol-4,1'-cyclopropane]; spiro[cholesta-5-en-3β,(24S)-diol-4,1'-cyclopropane]; spiro[cholesta-5-en-3β,25-diol-4,1'-cyclopropane]; spiro[(25R)-cholesta-5-en-3β,26-diol-4,1'-cyclopropane]; spiro[(25S)-cholesta-5-en-3β,26-diol-4,1'-cyclopropane]; spiro[cholesta-5,24-dien-3α,7β-diol-4,1'-cyclopropane]; spiro[cholesta-5,24-dien-3α,7α-diol-4,1'-cyclopropane]; spiro[cholesta-5,24-dien-3α,11β-diol-4,1'-cyclopropane]; spiro[cholesta-5,24-dien-3α,11α-diol-4,1'-cyclopropane]; spiro[cholesta-5,24-dien-3α,12β-diol-4,1'-cyclopropane]; spiro[cholesta-5,24-dien-3α,12α-diol-4,1'-cyclopropane]; spiro[cholesta-5,24-dien-3α,15β-diol-4,1'-cyclopropane]; spiro[cholesta-5,24-dien-3α,15α-diol-4,1'-cyclopropane]; spiro[cholesta-5,24-dien-3α,16β-diol-4,1'-cyclopropane]; spiro[cholesta-5,24-dien-3α,16α-diol-4,1'-cyclopropane]; spiro[cholesta-5,24-dien-3α,17β-diol-4,1'-cyclopropane]; spiro[cholesta-5,24-dien-3α,17α-diol-4,1'-cyclopropane]; spiro[cholesta-5,24-dien-3α,(20R)-diol-4,1'-cyclopropane]; spiro[cholesta-5,24-dien-3α,(20S)-diol-4,1'-cyclopropane]; spiro[cholesta-5,24-dien-3α,21-diol-4,1'-cyclopropane]; spiro[cholesta-5,24-dien-3α,(22R)-diol-4,1'-cyclopropane]; spiro[cholesta-5,24-dien-3α,(22S)-diol-4,1'-cyclopropane]; spiro[cholesta-5,24-dien-3α,(23R)-diol-4,1'-cyclopropane]; spiro[cholesta-5,24-dien-3α,(23S)-diol-4,1'-cyclopropane]; spiro[cholesta-5,24-dien-3α,26-diol-4,1'-cyclopropane]; spiro[cholesta-5,24-dien-3β,7α-diol-4,1'-cyclopropane]; spiro[cholesta-5,24-dien-3β,7α-diol-4,1'-cyclopropane]; spiro[cholesta-5,24-dien-3β,11β-diol-4,1'-cyclopropane]; spiro[cholesta-5,24-dien-3β,11α-diol-4,1'-cyclopropane]; spiro[cholesta-5,24-dien-3β,12β-diol-4,1'-cyclopropane]; spiro[cholesta-5,24-dien-3β,12α-diol-4,1'-cyclopropane]; spiro[cholesta-5,24-dien-3β,15β-diol-4,1'-cyclopropane]; spiro[cholesta-5,24-dien-3β,15α-diol-4,1'-cyclopropane]; spiro[cholesta-5,24-dien-3β,16β-diol-4,1'-cyclopropane]; spiro[cholesta-5,24-dien-3β,16α-diol-4,1'-cyclopropane]; spiro[cholesta-5,24-dien-3β,17β-diol-4,1'-cyclopropane]; spiro[cholesta-5,24-dien-3β,17α-diol-4,1'-cyclopropane]; spiro[cholesta-5,24-dien-3β,(20R)-diol-4,1'-cyclopropane]; spiro[cholesta-5,24-dien-3β,(20S)-diol-4,1'-cyclopropane]; spiro[cholesta-5,24-dien-3β,21-diol-4,1'-cyclopropane]; spiro[cholesta-5,24-dien-3β,(22R)-diol-4,1'-cyclopropane]; spiro[cholesta-5,24-dien-3β,(22S)-diol-4,1'-cyclopropane]; spiro[cholesta-5,24-dien-3β,(23R)-diol-4,1'-cyclopropane]; spiro[cholesta-5,24-dien-3β,(23S)-diol-4,1'-cyclopropane]; spiro[cholesta-5,24-dien-3β,26-diol-4,1'-cyclopropane]; 3α-hydroxycholesta-5-en-1-one; 3α-hydroxycholesta-5-en-2-one; 3α-hydroxycholesta-5-en-7-one; 3α-hydroxycholesta-5-en-11-one; 3α-hydroxycholesta-5-en-12-one; 3α-hydroxycholesta-5-en-15-one; 3α-hydroxycholesta-5-en-16-one; 3α-hydroxycholesta-5-en-22-one; 3α-hydroxycholesta-5-en-23-one; 3α-hydroxycholesta-5-en-24-one; 3β-hydroxycholesta-5-en-1-one; 3β-hydroxycholesta-5-en-2-one; 3β-hydroxycholesta-5-en-7-one; 3β-hydroxycholesta-5-en-11-one; 3β-hydroxycholesta-5-en-12-one; 3β-hydroxycholesta-5-en-15-one; 3β-hydroxycholesta-5-en-16-one; 3β-hydroxycholesta-5-en-22-one; 3β-hydroxycholesta-5-en-23-one; 3β-hydroxycholesta-5-en-24-one; 3α-hydroxycholesta-5,24-dien-1-one; 3α-hydroxycholesta-5,24-dien-2-one; 3α-hydroxycholesta-5,24-dien-7-one; 3α-hydroxycholesta-5,24-dien-11-one; 3α-hydroxycholesta-5,24-dien-12-one; 3α-hydroxycholesta-5,24-dien-15-one; 3α-hydroxycholesta-5,24-dien-16-one; 3α-hydroxycholesta-5,24-dien-22-one; 3α-hydroxycholesta-5,24-dien-23-one; 3β-hydroxycholesta-5,24-dien-1-one; 3β-hydroxycholesta-5,24-dien-2-one; 3β-hydroxycholesta-5,24-dien-7-one; 3β-hydroxycholesta-5,24-dien-11-one; 3β-hydroxycholesta-5,24-dien-12-one; 3β-hydroxycholesta-5,24-dien-15-one; 3β-hydroxycholesta-5,24-dien-16-one; 3β-hydroxycholesta-5,24-dien-22-one; 3β-hydroxycholesta-5,24-dien-23-one; 4,4-dimethyl-3α-hydroxycholesta-5-en-1-one; 4,4-dimethyl-3α-hydroxycholesta-5-en-2-one; 4,4-dimethyl-3α-hydroxycholesta-5-en-7-one; 4,4-dimethyl-3α-hydroxycholesta-5-en-11-one; 4,4-dimethyl-3α-hydroxycholesta-5-en-12-one; 4,4-dimethyl-3α-hydroxycholesta-5-en-15-one; 4,4-dimethyl-3α-hydroxycholesta-5-en-16-one; 4,4-dimethyl-3α-hydroxycholesta-5-en-22-one; 4,4-dimethyl-3α-hydroxycholesta-5-en-23-one; 4,4-dimethyl-3α-hydroxycholesta-5-en-24-one; 4,4-dimethyl-3β-hydroxycholesta-5-en-1-one; 4,4-dimethyl-3β-hydroxycholesta-5-en-2-one; 4,4-dimethyl-3β-hydroxycholesta-5-en-7-one; 4,4-dimethyl-3β-hydroxycholesta-5-en-11-one; 4,4-dimethyl-3β-hydroxycholesta-5-en-12-one; 4,4-dimethyl-3β-hydroxycholesta-5-en-15-one; 4,4-dimethyl-3β-hydroxycholesta-5-en-16-one; 4,4-dimethyl-3β-hydroxycholesta-5-en-22-one; 4,4-dimethyl-3β-hydroxycholesta-5-en-23-one; 4,4-dimethyl-3β-hydroxycholesta-5-en-24-one; 4,4-dimethyl-3α-hydroxycholesta-5,24-dien-1-one; 4,4-dimethyl-3α-hydroxycholesta-5,24-dien-2-one; 4,4-dimethyl-3α-hydroxycholesta-5,24-dien-7-one; 4,4-dimethyl-3α-hydroxycholesta-5,24-dien-11-one; 4,4-dimethyl-3α-hydroxycholesta-5,24-dien-12-one; 4,4-dimethyl-3α-hydroxycholesta-5,24-dien-15-one; 4,4-dimethyl-3α-hydroxycholesta-5,24-dien-16-one; 4,4-dimethyl-3α- hydroxycholesta-5,24-dien-22-one; 4,4-dimethyl-3α-hydroxycholesta-5,24-dien-23-one; 4,4-dimethyl-3β-hydroxycholesta-5,24-dien-1-one; 4,4-dimethyl-3β-hydroxycholesta-5,24-dien-2-one; 4,4-dimethyl-3β-hydroxycholesta-5,24-dien-7-one; 4,4-dimethyl-3β-hydroxycholesta-5,24-dien-11-one; 4,4-dimethyl-3β-hydroxycholesta-5,24-dien-12-one; 4,4-dimethyl-3β-hydroxycholesta-5,24-dien-15-one; 4,4-dimethyl-3β-hydroxycholesta-5,24-dien-16-one; 4,4-dimethyl-3β-hydroxycholesta-5,24-dien-22-one; 4,4-dimethyl-3β-hydroxycholesta-5,24-dien-23-one; spiro[3α-hydroxycholesta-5-en-7-one-4,1'-cyclopropane]; spiro[3α-hydroxycholesta-5-en-11-one-4,1'-cyclopropane]; spiro[3α-hydroxycholesta-5-en-12-one-4,1'-cyclopropane]; spiro[3α-hydroxycholesta-5-en-15-one-4,1'-cyclopropane]; spiro[3α-hydroxycholesta-5-en-16-one-4,1'-cyclopropane]; spiro[3α-hydroxycholesta-5-en-22-one-4,1'-cyclopropane]; spiro[3α-hydroxycholesta-5-en-23-one-4,1'-cyclopropane]; spiro[3α-hydroxycholesta-5-en-24-one-4,1'-cyclopropane]; spiro[3β-hydroxycholesta-5-en-7-one-4,1'-cyclopropane]; spiro[3β-hydroxycholesta-5-en-11-one-4,1'-cyclopropane]; spiro[3β-hydroxycholesta-5-en-12-one-4,1'-cyclopropane]; spiro[3β-hydroxycholesta-5-en-15-one-4,1'-cyclopropane]; spiro[3β-hydroxycholesta-5-en-16-one-4,1'-cyclopropane]; spiro[3β-hydroxycholesta-5-en-22-one-4,1'-cyclopropane]; spiro[3β-hydroxycholesta-5-en-23-one-4,1'-cyclopropane]; spiro[3β-hydroxycholesta-5-en-24-one-4,1'-cyclopropane]; spiro[3α-hydroxycholesta-5,24-dien-7-one-4,1'-cyclopropane]; spiro[3α-hydroxycholesta-5,24-dien-11-one-4,1'-cyclopropane]; spiro[3α-hydroxycholesta-5,24-dien-12-one-4,1'-cyclopropane]; spiro[3α-hydroxycholesta-5,24-dien-15-one-4,1'-cyclopropane]; Spiro[3α-hydroxycholesta-5,24-dien-16-one-4,1'-cyclopropane]; spiro[3α-hydroxycholesta-5,24-dien-22-one-4,1'-cyclopropane]; spiro[3β-hydroxycholesta-5,24-dien-7-one-4,1'-cyclopropane]; spiro[3β-hydroxycholesta-5,24-dien-11-one-4,1'-cyclopropane]; spiro[3β-hydroxycholesta-5,24-dien-12-one-4,1'-cyclopropane]; spiro[3β-hydroxycholesta-5,24-dien-15-one-4,1'-cyclopropane]; spiro[3β-hydroxycholesta-5,24-dien-16-one-4,1'-cyclopropane]; spiro[3β-hydroxycholesta-5,24-dien-22-one-4,1'-cyclopropane]; 4,4-dimethylcholest-5-en-1,3-dione; 4,4-dimethylcholest-5-en-3,7-dione; 4,4-dimethylcholest-5-en-3,11-dione; 4,4-dimethylcholest-5-en-3,12-dione; 4,4-dimethylcholest-5-en-3,15-dione; 4,4-dimethylcholest-5-en-3,16-dione; 4,4-dimethylcholest-5-en-3,22-dione; 4,4-dimethylcholest-5-en-3,23-dione; 4,4-dimethylcholest-5-en-3,24-dione; 4,4-dimethylcholest-5,24-dien-1,3-dione; 4,4-dimethylcholest-5,24-dien-3,7-dione; 4,4-dimethylcholest-5,24-dien-3,11-dione; 4,4-dimethylcholest-5,24-dien-3,12-dione; 4,4-dimethylcholest-5,24-dien-3,15-dione; 4,4-dimethylcholest-5,24-dien-3,16-dione; 4,4-dimethylcholest-5,24-dien-3,22-dione; 4,4-dimethylcholest-5,24-dien-3,23-dione; spiro[cholest-5-en-3,7-dione-4,1'-cyclopropane]; spiro[cholest-5-en-3,11-dione-4,1'-cyclopropane]; spiro[cholest-5-en-3,12-dione-4,1'-cyclopropane]; spiro[cholest-5-en-3,15-dione-4,1'-cyclopropane]; spiro[cholest-5-en-3,16-dione-4,1'-cyclopropane]; spiro[cholest-5-en-3,22-dione-4,1'-cyclopropane]; spiro[cholest-5-en-3,23-dione-4,1'-cyclopropane]; spiro[cholest-5-en-3,24-dione-4,1'-cyclopropane]; spiro[cholest-5,24-dien-3,7-dione-4,1'-cyclopropane]; spiro[cholest-5,24-dien-3,11-dione-4,1'-cyclopropane]; spiro[cholest-5,24-dien-3,2-dione-4,1'-cyclopropane]; spiro[cholest-5,24-dien-3,15-dione-4,1'-cyclopropane]; spiro[cholest-5-,24-dien-3,16-dione-4,1'-cyclopropane]; Spiro[cholest-5,24-dien-3,22-dione-4,1'-cyclopropane]; spiro[cholest-5,24-dien-3,23-dione-4,1'-cyclopropane]; 4,4-dimethyl-1β-hydroxycholesta-5-en-3-one; 4,4-dimethyl-1α-hydroxycholesta-5-en-3-one; 4,4-dimethyl-2β-hydroxycholesta-5-en-3-one; 4,4-dimethyl-2α-hydroxycholesta-5-en-3-one; 4,4-dimethyl-7β-hydroxycholesta-5-en-3-one; 4,4-dimethyl-7α-hydroxycholesta-5-en-3-one; 4,4-dimethyl-11β-hydroxycholesta-5-en-3-one; 4,4-dimethyl-11α-hydroxycholesta-5-en-3-one; 4,4-dimethyl-12β-hydroxycholesta-5-en-3-one; 4,4-dimethyl-12α-hydroxycholesta-5-en-3-one; 4,4-dimethyl-15β-hydroxycholesta-5-en-3-one; 4,4-dimethyl-15α-hydroxycholesta-5-en-3-one; 4,4-dimethyl-16β-hydroxycholesta-5-en-3-one; 4,4-dimethyl-16α-hydroxycholesta-5-en-3-one; 4,4-dimethyl-17β-hydroxycholesta-5-en-3-one; 4,4-dimethyl-17α-hydroxycholesta-5-en-3-one; 4,4-dimethyl-(20R)-hydroxycholesta-5-en-3-one; 4,4-dimethyl-(20S)-hydroxycholesta-5-en-3-one; 4,4-dimethyl-21-hydroxycholesta-5-en-3-one; 4,4-dimethyl-(22R)-hydroxycholesta-5-en-3-one; 4,4-dimethyl-(22S)-hydroxycholesta-5-en-3-one; 4,4-dimethyl-(23R)-hydroxycholesta-5-en-3-one; 4,4-dimethyl-(23S)-hydroxycholesta-5-en-3-one; 4,4-dimethyl-(24R)-hydroxycholesta-5-en-3-one; 4,4-dimethyl-(24S)-hydroxycholesta-5-en-3-one; 4,4-dimethyl-25-hydroxycholesta-5-en-3-one; 4,4-dimethyl-(25R)-26-hydroxycholesta-5-en-3-one; 4,4-dimethyl-(25S)-26-hydroxycholesta-5-en-3-one; 4,4-dimethyl-1β-hydroxycholesta-5,24-dien-3-one; 4,4-dimethyl-1α-hydroxycholesta-5,24-dien-3-one; 4,4-dimethyl-2β-hydroxycholesta-5,24-dien-3-one; 4,4-dimethyl-2α-hydroxycholesta-5,24-dien-3-one; 4,4-dimethyl-7β-hydroxycholesta-5,24-dien-3-one; 4,4-dimethyl-7α-hydroxycholesta-5,24-dien-3-one; 4,4-dimethyl-11β-hydroxycholesta-5,24-dien-3-one; 4,4-dimethyl-11α-hydroxycholesta-5,24-dien-3-one; 4,4-dimethyl-12β-hydroxycholesta-5,24-dien-3-one; 4,4-dimethyl-12α-hydroxycholesta-5,24-dien-3-one; 4,4-dimethyl-15β-hydroxycholesta-5,24-dien-3-one; 4,4-dimethyl-15α-hydroxycholesta-5,24-dien-3-one; 4,4-dimethyl-16β-hydroxycholesta-5,24-dien-3-one; 4,4-dimethyl-16α-hydroxycholesta-5,24-dien-3-one; 4,4-dimethyl-17β-hydroxycholesta-5,24-dien-3-one; 4,4-dimethyl-17α-hydroxycholesta-5,24-dien-3-one; 4,4-dimethyl-(20R)-hydroxycholesta-5,24-dien-3-one; 4,4-dimethyl-(20S)-hydroxycholesta-5,24-dien-3-one; 4,4-dimethyl-21-hydroxycholesta-5,24-dien-3-one; 4,4-dimethyl-(22R)-hydroxycholesta-5,24-dien-3-one; 4,4-dimethyl-(22S)-hydroxycholesta-5,24-dien-3-one; 4,4-dimethyl-(23R)-hydroxycholesta-5,24-dien-3-one; 4,4-dimethyl-(23S)-hydroxycholesta-5,24-dien-3-one; 4,4-dimethyl-26-hydroxycholesta-5,24-dien-3-one; spiro[7β-hydroxycholesta-5-en-3-one-4,1'-cyclopropane]; spiro[7α-hydroxycholesta-5-en-3-one-4,1'-cyclopropane]; spiro[11β-hydroxycholesta-5-en-3-one-4,1'-cyclopropane]; spiro[11α-hydroxycholesta-5-en-3-one-4,1'-cyclopropane]; spiro[12β-hydroxycholesta-5-en-3-one-4,1'-cyclopropane]; spiro[12α-hydroxycholesta-5-en-3-one-4,1'-cyclopropane]; spiro[15β-hydroxycholesta-5-en-3-one-4,1'-cyclopropane]; spiro[15α-hydroxycholesta-5-en-3-one-4,1'-cyclopropane]; spiro[16β-hydroxycholesta-5-en-3-one-4,1'-cyclopropane];

spiro[16α-hydroxycholesta-5-en-3-one-4,1'-cyclopropane]; spiro[17β-hydroxycholesta-5-en-3-one-4,1'-cyclopropane]; spiro[17α-hydroxycholesta-5-en-3-one-4,1'-cyclopropane]; spiro[(20R)-hydroxycholesta-5-en-3-one-4,1'-cyclopropane]; spiro[(20S)-hydroxycholesta-5-en-3-one-4,1'-cyclopropane]; spiro[21-hydroxycholesta-5-en-3-one-4,1'-cyclopropane]; spiro[(22R)-hydroxycholesta-5-en-3-one-4,1'-cyclopropane]; spiro[(22S)-hydroxycholesta-5-en-3-one-4,1'-cyclopropane]; spiro[(23R)-hydroxycholesta-5-en-3-one-4,1'-cyclopropane]; spiro[(23S)-hydroxycholesta-5-en-3-one-4,1'-cyclopropane]; spiro[(24R)-hydroxycholesta-5-en-3-one-4,1'-cyclopropane]; spiro[(24S)-hydroxycholesta-5-en-3-one-4,1'-cyclopropane]; spiro[25-hydroxycholesta-5-en-3-one-4,1'-cyclopropane]; spiro[(25R)-26-hydroxycholesta-5-en-3-one-4,1'-cyclopropane]; spiro[(25S)-26-hydroxycholesta-5-en-3-one-4,1'-cyclopropane]; spiro[7β-hydroxycholesta-5,24-dien-3-one-4,1'-cyclopropane]; spiro[7α-hydroxycholesta-5,24-dien-3-one-4,1'-cyclopropane]; spiro[11β-hydroxycholesta-5,24-dien-3-one-4,1'-cyclopropane]; spiro[11α-hydroxycholesta-5,24-dien-3-one-4,1'-cyclopropane]; spiro[12β-hydroxycholesta-5,24-dien-3-one-4,1'-cyclopropane]; spiro[12α-hydroxycholesta-5,24-dipn-3-one-4,1'-cyclopropane]; spiro[15β-hydroxycholesta-5,24-dien-3-one-4,1'-cyclopropane]; spiro[15α-hydroxycholesta-5,24-dien-3-one-4,1'-cyclopropane]; spiro[16β-hydroxycholesta-5,24-dien-3-one-4,1'-cyclopropane]; spiro[16α-hydroxycholesta-5,24-dien-3-one-4,1'-cyclopropane]; spiro[17β-hydroxycholesta-5,24-dien-3-one-4,1'-cyclopropane]; spiro[17α-hydroxycholesta-5,24-dien-3-one-4,1'-cyclopropane]; spiro[(20R)-hydroxycholesta-5,24-dien-3-one-4,1'-cyclopropane]; spiro[(20S)-hydroxycholesta-5,24-dien-3-one-4,1'-cyclopropane]; spiro[21-hydroxycholesta-5,24-dien-3-one-4,1'-cyclopropane]; spiro[(22R)-hydroxycholesta-5,24-dien-3-one-4,1'-cyclopropane]; spiro[(22S)-hydroxycholesta-5,24-dien-3-one-4,1'-cyclopropane]; spiro[(23R)-hydroxycholesta-5,24-dien-3-one-4,1'-cyclopropane]; spiro[(23S)-hydroxycholesta-5,24-dien-3-one-4,1'-cyclopropane]; and spiro[26-hydroxycholesta-5,24-dien-3-one-4,1'-cyclopropane].

Pharmaceutical Compositions

Pharmaceutical compositions comprising a compound of formula 1a or an ester thereof may further comprise carriers, diluents, absorption enhancers, preservatives, buffers, agents for adjusting the osmotic pressure, tablet disintegrating agents and other ingredients which are conventionally used in the art. Examples of solid carriers are magnesium carbonate, magnesium stearate, dextrin, lactose, sugar, talc, gelatin, pectin, tragacanth, methyl cellulose, sodium carboxymethyl cellulose, low melting waxes and cocoa butter.

Liquid compositions include sterile solutions, suspensions and emulsions. Such liquid compositions may be suitable for injection or for use in connection with ex vivo and in vitro fertilization. The liquid compositions may contain other ingredients which are conventionally used in the art, some of which are mentioned in the list above.

Further, a composition for transdermal administration of a compound of this invention may be provided in the form of a patch and a composition for nasal administration may be provided in the form of a nasal spray in liquid or powder form.

The dose of a compound of the invention to be used will be determined by a physician and will depend, inter alia, on the particular compound employed, on the route of administration and on the purpose of the use.

The compounds of formula 1a and esters thereof can be synthesized by methods known per se.

The present invention is further illustrated by the following examples which, however, are not to be construed as limiting the scope of protection. The features disclosed in the foregoing description and in the following examples may, in any combination thereof, be material for realizing the invention in diverse forms thereof.

EXAMPLES

Example 1

Testing of Cholest-5-en-3β,4β-diol as Meiosis Activating Substance in the Oocyte Test.

Animals

Oocytes were obtained from immature female mice (C57Bl/6J×DBA/2J F1-hybrids, Bomholtgaard, Denmark) weighing 13–16 grams, that were kept under controlled lighting and temperature. The mice received an intraperitoneal injection of 0.2 ml gonadotropins (Gonal-F, Serono, Solna, Sweden, containing 20 IU FSH, alternatively, Puregon, Organon, Swords, Ireland containing 20 IU FSH) and 48 hours later the animals were killed by cervical dislocation.

Collection and Culture of Oocytes

The ovaries were dissected out and the oocytes were isolated in Hx-medium (see below) under a stereo microscope by manual rupture of the follicles using a pair of 27 gauge needles. Spherical oocytes displaying an intact germinal vesicle (GV) were divided in cumulus enclosed oocytes (CEO) and naked oocytes (NO) and placed in α-minimum essential medium (α-MEM without ribonucleosides, Gibco BRL, Cat. No. 22561) supplemented with 3 mM hypoxanthine (Sigma Cat. No. H-9377), 8 mg/ml Human Serum Albumin (HSA, State Serum Institute, Denmark), 0.23 mM pyruvate (Sigma, Cat. No S-8636), 2 mM glutamine (Flow Cat. No. 16-801), 100 IU/mi penicillin and 100 μg/ml streptomycin (Flow, Cat No. 16-700). This medium was designated Hx-medium.

The oocytes were rinsed three times in Hx-medium and oocytes of uniform size were divided into groups of CEO and NO. CEO and NO were cultured in 4-well multidishes (Nunclon, Denmark) in which each well contained 0.4 ml of Hx-medium and 35–45 oocytes. One control (i.e., 35–45 oocytes cultured in Hx-medium with no addition of test compound) was always run simultaneously with the test cultures, which were made with different concentrations of the compounds to be tested as indicated in the tables below.

The cultures were performed at 37° C. and 100% humidity with 5% $CO_2$ in air. The culture time was 22–24 hours.

Examination of Oocytes

By the end of the culture period, the number of oocytes with germinal vesicle (GV) or germinal vesicle breakdown (GVB) and those with polar body (PB) was counted using a stereo microscope or an inverted microscope with differential interference contrast equipment. The percentage of oocytes with GVB per total number of oocytes and the percentage of oocytes with PB per total number of oocytes was calculated in the test cultures and compared to the control culture.

Activation of meiosis in oocytes using cholest-5-en-3β, 4β-diol. Source of compound: Steraloids Inc., Wilton, N.H., USA, Cat. No. C 6410, Batch No. L1066. The results are given in the tables below:

| NO: | | |
|---|---|---|
| % GVB | % PB | Test concentration $\mu M$ |
| 18.6 | 1.7 | control |
| 50.2 | 17.2 | 7.0 |

| CEO: | | |
|---|---|---|
| % GVB | % PB | Test concentration $\mu M$ |
| 27.0 | 10.8 | control |
| 44.4 | 25.9 | 7.0 |

As it appears from the tables, cholest-5-en-3β,4β-diol induces meiosis in both naked and cumulus enclosed oocyte when cultured in vitro.

Example 2

Test of Meiosis Inhibiting Substances in the Oocyte Test.

Germinal vesicle (GV) oocytes were obtained from immature FSH treated female mice using the same methods as described in Example 1 (see above). The oocytes were rinsed three times in Hx-medium and oocytes of uniform size were divided into groups of CEO and NO. 4,4-Dimethylcholest-8,14,24-trien-3β-ol (FF-MAS) has previously been shown to induce meiosis in CEO and NO in vitro (Byskov, A. G. et al. *Nature* 374 (1995) 559–562). CEO and NO were cultured in Hx-medium supplemented with 0.7–7.0 $\mu M$ FF-MAS in co-culture with the test compounds in different concentrations in 4-well multidishes (Nunclon, Denmark) in which each well contained 0.4 ml of Hx-medium and 35–45 oocytes. One control (i.e., 35–45 oocytes cultured in Hx-medium containing FF-MAS with no addition of test compound) was always run simultaneously with the test cultures, which were supplemented with different concentrations of the compounds to be tested.

Test results for the inhibition of meiosis in oocytes using cholest-5-en-3β,(22R)-diol (in the following designated "22R") are given in the tables below:

| NO: | | | | |
|---|---|---|---|---|
| % GVB | % PB | FF-MAS concentration $\mu M$ | 22R concentration $\mu M$ | Concentration ratio FF-MAS:22R |
| 19.5 | 9.5 | 1.2 | — | Control |
| 4.6 | 0 | 1.2 | 25 | 1:20 |
| 33.0 | 7.8 | 0.7 | — | Control |
| 16.9 | 0 | 0.7 | 13 | 1:19 |
| 2.9 | 0 | 0.7 | 25 | 1:36 |

| CEO: | | | | |
|---|---|---|---|---|
| % GVB | % PB | FF-MAS concentration $\mu M$ | 22R concentration $\mu M$ | Concentration ratio FF-MAS:22R |
| 21.7 | 10.8 | 0.7 | — | Control |
| 6.9 | 3.4 | 0.7 | 25 | 1:36 |
| 39.0 | 18.9 | 7 | — | Control |
| 21 | 3.5 | 7 | 12.5 | 1:2 |

As it appears from the tables, 22R antagonises the FF-MAS induced resumption of meiosis in a dose-related manner.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are embraced therein.

Example 3

4,4-dimethylcholesta-5,8-diene-3-one

The D-8-double bond is introduced as described in the literature [J. Lip. Res. 37, 1529, (1996)]. According to the literature procedure, cholesta-5,8-diene-3β-ol is prepared in a three step sequence. This alcohol is oxidized in a classical Oppenauer oxidation [Helv. Chim. Acta 22, 1178, (1939)] to give cholesta-4,8-diene-3-one. This ketone is used as a starting material for some of the following compounds.

Potassium tert-butylate (550 mg) is dissolved in 13 ml tert-Butanol at 45° C. A solution of cholesta-4,8-diene-3-one (470 mg) in 1.5 ml tetrahydrofuran is added dropwise. After 10 minutes, methyliodide (0,63 ml) is added. The reaction mixture is stirred for one hour. After aqueous work-up and column chromatography, 4,4-dimethyl-cholesta-5,8-diene-3-one (310 mg) is isolated.

$^1$H-NMR (CDCl$_3$): δ=0.64 ppm (s, 3H, H-18); 0.86 (2×d, J=7 Hz, 6H, H-26/27); 0.94 (d, J=7 Hz, 3H, H-21); 1.04 (s, 3H, H-19); 1.24 (s, 3H, 4–CH$_3$); 1.29 (s, 3H, 4–CH$_3$); 2.63 (m, 2H, H-7); 5.69 (t, J=3 Hz, 1H, H-6). C$_{29}$H$_{46}$=, MW (Molecular Weight): 410.684.

Example 4

4,4-dimethylcholesta-5,8-diene-3β-ol 4,4-Dimethylcholesta-5,8-diene-3-one (100 mg) is reduced with lithiumalurninumhydride (5 mg) in 2 ml tetrahydrofuran at room temperature. The solution is stirred for one hour. After aqueous work-up and column chromatography 4,4-dimethylcholesta-5,8-diene-3β-ol (60 mg) is isolated.

$^1$H-NMR (CDCl$_3$): δ=0.63 ppm (s, 3H, H-18); 0.86 (s×d, J=7 Hz, 6H, H-26/27); 0.94 (d, J=7 Hz, 3H, H-21); 1.12 (s, 3H, H-19); 1.15 (s, 3H, 4–CH$_3$) 1.21 (s, 3H, 4–CH$_3$); 2.56 (m, 2H, H-7); 3.82 (dd, J=10 Hz, J=5 Hz, 1H H-3); 5.75 (t, J=3 Hz, 1H, H-6). C$_{29}$H$_{48}$O, MW: 412.700.

Example 5

Cholesta-5,8-diene-3β-yl Acetate $^1$H-NMR (CDCl$_3$): δ=0.64 ppm (s, 3H, H-18); 0.87 (2×d, J=7 Hz, 6H, H-26/27); 0.94 (d, J=7 Hz, 3H, H-21); 1.20 (s, 3H, H-19); 2.03 (s, 3H, 3-OAc) 2.28 (m, 2H, H-4); 2.53 (m, H-7); 4.61 (m, 1H, H-3); 5.45 (m, 1H, H-6). C$_{29}$H$_{46}$O$_2$, MW: 426.683. J. Lipid Res. 37, 1529, (1996).

Example 6
5β-cholest-8-ene-3β,5β-diol

Cholesta-5,8-diene-3-on is epoxidized in analogy to a literature procedure [J. Med. Chem. 39, 5092, (1996)] to give 4α,5-epoxy-5α-cholest-8-en-3-on. This is reduced as described below.

4α,5-Epoxy-5α-cholest-8-en-3-on (75 mg) is dissolved in 3 ml tetrahydrofuran. Lithiumaluminumhydride (30 mg) is added at room temperature. The reaction mixture is stirred for 15 hours. After aqueous work-up and column chromatography 5β-cholest-8-ene-3β,5β-diol (19 mg) and 5β-cholest-8-ene-3α,5β-diol (24 mg) are isolated.

$^1$H-NMR (CDCl$_3$): δ=0.63 ppm (s, 3H, H-18); 0.86 (2×d, J=7 Hz, 6H, H-26/27); 0.94 (d, J=7 Hz, 3H, H-21); 1.06 (s, 3H, H-19); 2.53 (broad, 1H, OH) 4.09 (m, 1H, H-3). C$_{27}$H$_{46}$O$_2$, MW: 402.661.

Example 7
5β-cholest-8-ene-3α,5β-diol $^1$H-NMR (CDCl$_3$): δ=0.63 ppm (s, 3H, H-18); 0.87 (2×d, J=7 Hz, 6H, H-26/27); 0.94 (d, J=7 Hz, 3H, H-21); 0.99 (s, 3H, H-19); 3.97 (m, 1H, H-3). C$_{27}$H$_{46}$O$_2$, MW: 402.661.

Example 8
4,4-dimethylcholesta-5,7,14-triene-3-one $^1$H-NMR (CDCl$_3$): δ=0.87 (2×d, J=7 Hz, 6H, H-26/27); 0.94 (s, H3); 0.95 (d, J=7 Hz, 3H, H-21); 1.09 (s, 3H); 1.17 (s, 3H, 4–CH$_3$); 1.36 (s, 3H, 4–CH$_3$); 5.69 (s, 1H, H-14); 6.05 (d, J=10 Hz, 1H, H-7); 6.57 (d, J=10 Hz, 1H, H-6); C$_{29}$H$_{44}$O, MW: 408.668. J. Chem. Soc. P.T. 1, 812, (1977).

Example 9
3β-(acetyloxy)-5α-cholest-8-ene-6α-ol

Cholesta-5,8-diene-3β-yl acetate (1.0 g) is dissolved in 250 ml diethylether. The reaction mixture is cooled to 0° C. and 2.35 ml of borane-dimethylsulphide-complex (2 M solution in tetrahydrofuran) is added. The reaction mixture is warmed to room temperature within 2 hours. Then, 26 ml water, 26 ml sodium hydroxyde solution (10% aqueous) and 3.65 ml hydrogen-peroxyde (30%) are added at 0° C. After aqueous work-up and column chromatography 3β-(acetyloxy)-5α-cholest-8-ene-6α-ol (140 mg) is isolated.

$^1$H-NMR (CDCl$_3$):δ=0.59 ppm (s, 3H, H-18); 0.87 (2×d, J=7 Hz, 6H, H-26/27); 0.94 (d, J=7 Hz, 3H, H-21); 0.99 (s, H3, H-19); 2.03 (s, 3H, 3-OAc); 2.26 (m, 1H); 2.48 (m, 1H); 3.72 (m, 1H, H-6); 4.69 (m, 1H, H-3); C$_{29}$H$_{48}$O$_3$, MW: 444.698.

Example 10
5α-cholest-7-ene-3β,5α,6β-triol $^1$H-NMR (CDCl$_3$): δ=0.59 ppm (s, 3H, H-18); 0.87 (2×d, J=7 Hz, 6H, H-26/27); 0.94 (d, J=7 Hz, 3H, H-21); 1.08 (s, H3, H-19); 3.63 (m, 1H, H-6); 4.08 (m, 1H, H-3); 5.35 (m, 1H, H-7). C$_{27}$H$_{46}$O$_3$, MW: 418.660. J. Org. Chem. 50, 1835, (1985).

Example 11
Cholesta-5,8,14-triene-3β-ol

Cholesta-5,8-diene-3β-ol (1.54 g) is dissolved in 50 ml dichloromethane. A solution of m-chloroperoxybenzoic acid (1.04 g) in 50 ml dichloromethane is added at room temperature. The reaction mixture is stirred for 5 hours.

After aqueous work-up and subsequent column chromatography 8α,9α-epoxycholest-5-en-3β-ol (740 mg) is isolated.

8α,9α-Epoxycholest-5-en-3β-ol (200mg) is dissolved in dichloromethane and the solution is cooled to 0° C. 1.5 ml of a diethylaluminumcyanide-solution (1 M in toluene) is added dropwise. After addition, the reaction mixture is warmed to room temperature and stirred for additional 18 hours. After basic work-up and column chromatography, cholesta-5,8,14-triene-3β-ol (51 mg) is isolated.

$^1$H-NMR (CDCl$_3$): δ=0.84 ppm (s, 3H, H-18); 0.86 (2×d, J=7 Hz, 6H, H-26/27); 0.94 (d, J=7 Hz, 3H, H-21); 1.22 (s, H3, H-19); 2.59 (m, 1H, H-7); 2.88 (m, 1H, H-7); 3.57 (m, 1H, H-3); 5.38 (m, 1H, H-15); 5.52 (m, 1H, H-6). C$_{27}$H$_{42}$O, MW: 382.630.

Example 12
1α-hydroxy-5β-cholestane-3-one $^1$H-NMR (CDCl$_3$): δ=0.68 ppm (s, 3H, H-18); 0.86 (2×d, J=7 Hz, 6H, H-26/27); 0.90 (d, J=7 Hz, 3H, H-21); 1.21 (s, H3, H-19); 3.62 (m, 1H, H-1). C$_{27}$H$_{46}$O$_2$, MW: 402.661. J. Chem. Soc. P.T. 1, 2488, (1977).

Example 13
Cholest-5-ene-3β-9α-diol

8α,9α-Epoxycholest-5-en-3β-ol (200 mg) is dissolved in 13 ml diethylamine at −20° C. Lithium (100 mg) is added in small portions. The reaction mixture is stirred for 3 hours. After aqueous work-up, a crude product (207 mg) is isolated. Crystallization from diisopropylether yields cholest-5-ene-3β,9α-diol (62 mg).

$^1$H-NMR (CDCl$_3$): δ=0.68 ppm (s, 3H, H-18); 0.86 (2×d, J=7 Hz, 6H, H-26/27); 0.93 (d, J=7 Hz, 3H, H-21); 1.15 (s, H3, H-19); 2.37 (m, 1H); 3.52 (m, 1H, H-3); 5.40 (m, 1H, H-6). C$_{27}$H$_{46}$O$_2$, MW: 402.661.

Example 14
5α-cholest-7-ene-3β-5α-diol $^1$H-NMR (CDCl$_3$): δ=0.56 ppm (s, 3H, H-18); 0.86 (2×d, J=7 Hz, 6H, H-26/27); 0.92 (s, 3H, H-19); 0.94 (d, J=7 Hz, 3H, H-21); 2.24 (m, 1H); 4.05 (m, 1H, H-3); 5.08 (m, 1H, H-7). C$_{27}$H$_{48}$O$_2$, MW: 402.661. Biochem. J. 105,1194, (1967).

Example 15
5α-cholestane-1α-3α-diol

1α-Hydroxy-5β-cholestane-3-one [J. Chem. Soc. Perkin. Trans. 1, 1977, 2488] (110 mg) is dissolved in 6 ml ethanol.

Sodiumborohydride (52 mg) is added at room temperature in one portion. The reaction mixture is stirred for 4 hours. After aqueous work-up and column chromatography, 5β-Cholestane-1α,3α-diol (75 mg) is isolated.

$^1$H-NMR (CDCl$_3$): δ=0.64 ppm (s, 3H, H-18); 0.86 (2×d, J=7 Hz, 6H, H-26/27); 0.88 (d, J=7 Hz, 3H, H-21); 1.12 (s, 3H, H-19); 3.29 (dd, J=12 Hz, J=3 Hz, 1H, H-1); 3.77 (m, 1H, H-3). C$_{27}$H$_{48}$O$_2$, MW: 404.677.

Example 16
5α-cholestane-3β-5β-diol $^1$H-NMR (CDCl$_3$): δ=0.65 ppm (s, 3H, H-18); 0.86 (2×d, J=7 Hz, 6H, H-26/27); (d, J=7 Hz, 3H, H-21); 0.95 (s, 3H, H-19); 2.01 (m, 1H, H-4); 2.20 (dd, J=15 Hz, J=4 Hz, 1H, H-4); 3.00 (broad, 1H, OH); 4.13 (m, 1H, H-3). C$_{27}$H$_{48}$O$_2$, MW: 404.677. J. Org. Chem. 27, 1433, (1962).

Example 17
5β-cholestane-3α-5β-diol $^1$H-NMR (CDCl$_3$): δ=0.64 ppm (s, 3H, H-18); 0.86 (2×d, J=7 Hz, 6H, H-26/27); 0.89 (s, 3H, H-19); 0.91 (d, J=7 Hz, 3H, H-21); 4.02 (m,1H. H-3). C$_{27}$H$_{48}$O$_2$, MW: 404.677. J. Org. Chem. 27,1433, (1962).

Example 18
5α-cholestane-3α-5α-diol $^1$H-NMR (CDCl$_3$): δ=0.65 ppm (s, 3H, H-18); 0.86 (2×d, J=7 Hz, 6H, H-26/27); 0.92 (d, J=7 Hz, 3H, H-21); 0.95 (s, 3H, H-19); 3.25 (broad, 1H, OH); 4.10 (m, 1H, H-3). C$_{27}$H$_{48}$O$_2$, MW: 404.677. J. Chem. Soc., 4482, (1961).

Example 19
3β-(benzoyloxy)-22-hydroxy-4,4-dimethyl-5α-cholest-8(14)-ene-15,24-dione $^1$H-NMR (CDCl$_3$): δ=0.85 ppm (s, 3H, H-18); 0.96–1-16 (m, 18H, H-19, H-21, 2×4–CH$_3$, H-26/27); 2.6 (m, 1H, H-25); 3.3 (d, J=2 Hz, 1H, 22-OH); 4.06 (m, 1H. H-22); 4.22 (m, 1H, H-7); 4.8 (dd, J=11 Hz, J=5 Hz, 1H, H-3). C$_{36}$H$_{50}$O$_5$, MW: 562.790. J. Am. Chem. Soc. 11 (1989), 278.

Example 20
3β-(benzoyloxy)-4,4-dimethyl-5α-cholest-8(14)-ene-15,24-dione $^1$H-NMR (CDCl$_3$): δ=0.85 ppm (s, 3H, H-18); 0.97–1-14 (m, 18H, 2×4–CH$_3$, H-19, H-21, H-26/27); 2.6 (m, 1H, H-25); 4.21 (m, 1H, H-7); 4.8 (dd, J=11 Hz, J=5 Hz, 1H, H-3). C$_{36}$H$_{50}$O$_4$, MW: 546.791. J. Am. Chem. Soc. 11 (1989), 278.

Example 21
3β-(benzoyloxy)-24-hydroxy-4,4-dimethyl-5α-cholest-8(14)-ene-15-one $^1$H-NMR (CDCl$_3$): δ=0.85 ppm (s, 3H, H-18); 0.88–1-04 (m, 18H, H-19, H-21, 2×4-CH$_3$, H-26/27); 2.38 (m, 1H, H-16); 3.31 (m, 1H, H-24); 4.21 (m, 1H, H-7); 4.8 (dd, J=11 Hz, J=5 Hz, 1H, H-3). C$_{36}$H$_{52}$O$_4$, MW: 548.807. J. Am. Chem. Soc. 11 (1989), 278.

Example 22
5β-cholest-7-ene-3β,5β-diol 5,6β-Epoxy-5β-cholest-7-en-3β-ol [J. Org. Chem. 50 (1985), 1835] (150 mg) is dissolved in 2.5 ml of a potassium hydroxyde solution (5% in methanol). The reaction mixture is refluxed for one hour. Aqueous work-up, extraction with ethylacetate and column chromatography yields 5β-cholest-7-ene-3β,5β-diol (54 mg).

$^1$H-NMR (CDCl$_3$): δ=0.55 ppm (s, 3H, H-18); 0.86 (2×d, J=7 Hz, 9H, H-26/27); 0.92 (s, 3H, H-19); 0.94 (d, J=7 Hz, 3H, H-21); 4.16 (m, 1H, H-3); 5.05 (m, 1H, H-7). C$_{27}$H$_{46}$O$_2$, MW: 402.661.

Example 23
5β-cholest-6-ene-3β,5β,8β-triol $^1$H-NMR (CDCl$_3$): δ=0.66 ppm (s, 3H, H-18); 0.87 (3×d, J=7 Hz, 9H, H-21/26/27); 1.28 (s, 3H, H-19); 2.24 (m, 1H); 2.77 (m, 1H); 3.48 (m, 1H, H-3); 5.64 (d, J=11 Hz, 1H); 5.88 (d, J=11 Hz, 1H). C$_{27}$H$_{46}$O$_3$, MW: 418.660. J. Org. Chem. 50 (1961), 1835,.

Example 24
5α-cholest-8-ene-3β,6α-diol $^1$H-NMR (CDCl$_3$): δ=0.60 ppm (s, 3H, H-18); 0.87 (2×d, J=7 Hz, 6H, H-26/27); 0.94 (d, J=7 Hz, 3H, H-21); 0.98 (s, 3H, H-19); 2.48 (m, 1H); 3.62 (m, 1H, H-3); 3.75 (m, 1H, H-6). C$_{27}$H$_{46}$O$_2$, MW: 402.661. Proc. Chem. Soc. London, 450, (1961).

Example 25
5β-cholest-8-ene-3β,6β-diol

3β-(Acetyloxy)-5α-cholest-8-ene-6α-ol (124 mg) is dissolved in 20 ml ethanol. Solid potassium hydroxyde (710 mg) is added and the reaction mixture is stirred for 2 hours. After aqueous work-up, 5β-cholest-8-ene-3β,6β-diol (96 mg) is isolated.

$^1$H-NMR (CDCl$_3$): δ=0.65 ppm (s, 3H, H-18); 0.87 (2×d, J=7 Hz, 6H, H-26/27); 0.93 (d, J=7 Hz, 3H, H-21); 1.14 (s, 3H, H-19); 2.33 (m, 2H); 3.83 (m, 2H, H-3/6). C$_{27}$H$_{46}$O$_2$, MW: 402.661.

Example 26
(24R,S)-4,4-dimethyl-5α-cholesta-8,14-dien-3β,24-diol $^1$H-NMR (CDCl$_3$): 5.36 ppm (s, 1H); 3.33 (m, 1H); 3.23 (dd, 1H); 1.05 (s, 3H); 1.02 (s, 3H); 0.92 (m, 9H); 0.84 (s, 3H); 0.81 (s, 3H).

This compound was separated into the (24R) and the (24S) isomers.

What is claimed is:

1. A method of regulating meiosis in a mammalian germ cell comprising administering to a germ cell in need thereof an effective amount of a compound of formula 1c:

wherein R$^1$ and R$^2$, which are different or identical provided that they are not both hydroxy, are hydrogen, halogen, hydroxy or branched or unbranched C$_1$–C$_6$ alkyl which may be substituted by halogen, hydroxy or cyano, or wherein R$^1$ and R$^2$ together designate methylene or oxo or, together with the carbon atom to which they are bound, form a cyclopropane ring, a cyclopentane ring, or a cyclohexane ring; R$^3$ is hydrogen, methylene, hydroxy, methoxy, acetoxy, oxo, halogen, C$_1$–C$_4$ alkandiyl (bound to the same carbon atom of the sterol skeleton) or =NOR$^{26}$ wherein R$^{26}$ is hydrogen or C$_1$–C$_3$ alkyl, or R$^3$ designates, together with R$^9$ or R$^{14}$, an additional bond between the carbon atoms at which R$^3$ and R$^9$ or R$^{14}$ are placed; R$^4$ is hydrogen, methylene, hydroxy, methoxy, acetoxy, oxo, halogen, C$_1$–C$_4$ alkandiyl (bound to the same carbon atom of the sterol skeleton) or =NOR$^{27}$ wherein R$^{27}$ is hydrogen or C$_1$–C$_3$ alkyl, or R$^4$ designates, together with R$^{13}$ or R$^{15}$, an additional bond between the carbon atoms at which R$^4$ and R$^{13}$ or R$^{15}$ are placed; R$^5$ is hydrogen, halogen, C$_1$–C$_4$ alkyl, methylene, hydroxy, methoxy, oxo or =NOR$^{22}$ wherein R$^{22}$ is hydrogen or C$_1$–C$_3$ alkyl, or R$^5$ designates, together with R$^6$ an additional bond between the carbon atoms at which R$^5$ and R$^6$ are placed; R$^6$ is hydrogen or hydroxy or R$^6$ designates, together with R$^5$, an additional bond between the carbon atoms at which R$^5$ and R$^6$ are placed; R$^9$ is hydrogen, hydroxy, halogen or oxo or R$^9$ designates, together with R$^3$ or R$^{10}$, an additional bond between the carbon atoms at which R$^9$ and R$^3$ or R$^{10}$ are placed; R$^{10}$ is hydrogen, halogen or hydroxy, or R$^{10}$ designates, together with R$^9$, an additional bond between the carbon atoms at which R$^{10}$ and R$^9$ are placed; R$^{11}$ is hydroxy, optionally substituted alkoxy, acyloxy, sulphonyloxy, phosphonyloxy, oxo, halogen, C$_1$–C$_4$ alkandiyl (bound to the same carbon atom of the sterol skeleton) or =NOR$^{28}$ wherein R$^{28}$ is hydrogen or C$_1$–C$_3$ alkyl, or R$^{11}$ designates, together with R$^{12}$, an additional bond between the carbon atoms at which $R^{11}$ and $R^{12}$ are placed; $R^{12}$ is hydrogen, hydroxy, $C_1$–$C_3$ alkyl, vinyl, $C_1$–$C_3$ alkoxy or halogen, or $R^{12}$ designates, together with $R^{11}$, an additional bond between the carbon atoms at which $R^{12}$ and $R^{11}$ are placed; $R^{13}$ is hydrogen, hydroxy or halogen or $R^{13}$ designates together with $R^4$ or $R^{14}$, an additional bond between the carbon atoms at which $R^{13}$ and $R^4$ or $R^{14}$ are placed; $R^{14}$ is hydrogen, hydroxy or halogen, or $R^{14}$ designates, together with $R^3$, $R^6$ or $R^{13}$, an additional bond between the carbon atoms at which $R^{14}$ and $R^3$ or $R^6$ or $R^{13}$ are placed; $R^{15}$ is hydrogen, halogen, $C_1$–$C_4$ alkyl, methylene, hydroxy, methoxy, acetoxy, oxo or =$NOR^{23}$ wherein $R^{23}$ is hydrogen or $C_1$–$C_3$ alkyl, or $R^{15}$ designates together with $R^4$, an additional bond between the carbon atoms at which $R^{15}$ and $R^4$ are placed; $R^{16}$ is hydrogen, halogen, $C_1$–$C_3$ alkyl, methylene, hydroxy, methoxy, oxo or =$NOR^{24}$ wherein $R^{24}$ is hydrogen or $C_1$–$C_3$ alkyl, or $R^{16}$ designates, together with $R^{17}$, an additional bond between the carbon atoms at which $R^{16}$ and $R^{17}$ are placed; $R^{17}$ is hydrogen or hydroxy, or $R^{17}$ designates, together with $R^{16}$, an additional bond between the carbon atoms at which $R^{17}$ and $R^{16}$ are placed; $R^{18}$ and $R^{19}$ are both hydrogen, or one of $R^{18}$ and $R^{19}$ is hydrogen while the other is halogen, hydroxy or methoxy, or $R^{18}$ and $R^{19}$ together designate oxo; $R^{25}$ is $C_1$–$C_4$ alkyl or hydroxymethyl, or $R^{25}$ and $R^{31}$ together designate methylene or oxo; $R^{29}$ is hydrogen, halogen, methyl, hydroxy or oxo; $R^{30}$ is hydrogen, halogen, methyl, or hydroxy; $R^{31}$ is hydrogen, halogen, methyl or hydroxy, or $R^{31}$ together with $R^{25}$, designates methylene or oxo; and A is a carbon atom or a nitrogen atom; and when A is a carbon atom, $R^7$ is hydrogen, hydroxy or halogen; and $R^8$ is hydrogen, halogen, hydroxy, $C_1$–$C_4$ alkyl, methylene or oxo, or $R^7$ designates, together with $R^8$, an additional bond between the carbon atoms at which $R^7$ and $R^8$ are placed; $R^{20}$ is $C_1$–$C_4$ alkyl, trifluoromethyl and $C_3$–$C_6$ cycloalkyl; $R^{21}$ is $C_1$–$C_4$ alkyl, $C_1$–$C_4$ hydroxyalkyl, $C_1$–$C_4$ haloalkyl containing up to three halogen atoms, methoxymethyl, acetoxymethyl, and $C_3$–$C_6$ cycloalkyl, or $R^{20}$ and $R^{21}$, together with the carbon atom at which they are placed, form a $C_3$–$C_6$ cycloalkyl ring; and when A is a nitrogen atom, $R^7$ designates a lone pair of electrons; and $R^8$ is hydrogen, hydroxy, $C_1$–$C_4$ alkyl, cyano and oxo; and $R^{20}$ and $R^{21}$ are independently, $C_1$–$C_4$ alkyl or $C_3$–$C_6$ cycloalkyl; provided that at least one of $R^1$, $R^2$, $R^6$, $R^8$, $R^9$, $R^{10}$, $R^{12}$, $R^{13}$, $R^{14}$, $R^{18}$, $R^{19}$, $R^{29}$, $R^{30}$ and $R^{31}$ is hydroxy or $R^{25}$ is hydroxymethyl, and further provided that $R^9$, $R^{10}$ and $R^{11}$ are not all hydroxy.

2. The method of claim 1 wherein the compound is administered to the germ cell by administering it to a mammal hosting the germ cell.

3. The method according to claim 1 wherein the germ cell is an oocyte.

4. The method according to claim 1 wherein the compound is administered to an oocyte ex vivo.

5. The method according to claim 1 wherein the germ cell is a male germ cell.

6. The method according to claim 1 whereby mature male germ cells are produced by administering a compound of claim 3 to testicular tissue in vivo or in vitro.

* * * * *

UNITED STATES PATENT AND TRADEMARK OFFICE
CERTIFICATE OF CORRECTION

PATENT NO. : 6,759,400 B2 Page 1 of 1
APPLICATION NO. : 10/242381
DATED : July 6, 2004
INVENTOR(S) : Grondahl et al.

It is certified that error appears in the above-identified patent and that said Letters Patent is hereby corrected as shown below:

Column 38, line 28, claim 6: delete "a compound of".
Column 38, line 28, claim 6: after "administering" add --said compound--.
Column 38, line 29, claim 6: delete "claim 3".

Signed and Sealed this

Thirty-first Day of July, 2007

JON W. DUDAS
*Director of the United States Patent and Trademark Office*